(12) United States Patent
Krulevitch et al.

(10) Patent No.: US 11,574,562 B2
(45) Date of Patent: Feb. 7, 2023

(54) DEVICES AND METHODS FOR DRUG ADMINISTRATION AND MIXING, AND TRAINING OF PROPER TECHNIQUES THEREFOR

(71) Applicant: Janssen Pharmaceutica NV, Beerse (BE)

(72) Inventors: Peter A. Krulevitch, Pleasanton, CA (US); Ian Scrimgeour, Dunbar (GB); Scott Martin, Edinburgh (GB); James McLusky, Edinburgh (GB); James Glencross, Edinburgh (GB); Blair Hutton, Edinburgh (GB); Nick Foley, Edinburgh (GB); Jose Antonio Buron Vidal, Parede (PT)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/081,549

(22) Filed: Oct. 27, 2020

(65) Prior Publication Data

US 2021/0043111 A1    Feb. 11, 2021

Related U.S. Application Data

(63) Continuation of application No. 15/736,362, filed as application No. PCT/EP2016/064229 on Jun. 20, 2016, now Pat. No. 10,861,351.

(Continued)

(51) Int. Cl.
*G09B 23/28*       (2006.01)
*A61J 1/20*        (2006.01)
(Continued)

(52) U.S. Cl.
CPC ............... *G09B 23/28* (2013.01); *A61J 1/16* (2013.01); *A61J 1/2055* (2015.05); *A61J 1/2096* (2013.01);
(Continued)

(58) Field of Classification Search
CPC ........ G09B 23/28; G09B 5/02; G09B 23/285; A61J 1/2055; A61J 1/16; A61J 1/2096;
(Continued)

(56) References Cited

U.S. PATENT DOCUMENTS 6,039,557 A    3/2000   Unger et al.
6,332,704 B1   12/2001  Gasser et al.
(Continued)

FOREIGN PATENT DOCUMENTS

CN   101218611    7/2008
CN   102123751    7/2011
(Continued)

OTHER PUBLICATIONS

International Search Report dated Nov. 17, 2015; International Application No. PCT/US2015/036969.
(Continued)

*Primary Examiner* — Robert P Bullington
(74) *Attorney, Agent, or Firm* — Xu Ming Ming Chen

(57) ABSTRACT

A device for training users in a proper mixing of pharmaceutical components, or for aiding in the mixing, or for performing the mixing, and administration of pharmaceutical components is disclosed. The device comprises a housing for receiving a pharmaceutical delivery device containing the pharmaceutical components. There is also a microcontroller disposed in the housing and a motion/orientation detection device disposed within or on the housing and in communication with the microcontroller. A (Continued)

method for use of the device is also disclosed, along with a substance for use as one of the pharmaceutical components.

20 Claims, 27 Drawing Sheets

Related U.S. Application Data

(60) Provisional application No. 62/182,426, filed on Jun. 19, 2015.

(51) Int. Cl.
*A61J 1/16* (2006.01)
*G09B 5/02* (2006.01)
*A61J 7/00* (2006.01)
*A61M 5/178* (2006.01)

(52) U.S. Cl.
CPC .......... *A61J 7/0053* (2013.01); *A61M 5/1782* (2013.01); *G09B 5/02* (2013.01); *G09B 23/285* (2013.01); *A61J 2200/70* (2013.01); *A61M 2205/50* (2013.01); *A61M 2205/581* (2013.01)

(58) Field of Classification Search
CPC .. A61J 7/0053; A61J 2200/70; A61J 2205/50; A61J 2205/581; A61M 5/1782
See application file for complete search history.

(56) References Cited

U.S. PATENT DOCUMENTS

| | | | |
|---|---|---|---|
| 6,626,912 B2 | 9/2003 | Speitling | |
| 7,591,801 B2 | 9/2009 | Brauker et al. | |
| 8,032,251 B2 | 10/2011 | Monn | |
| 8,118,776 B2 | 2/2012 | Lampropoulos et al. | |
| 8,556,867 B2 | 10/2013 | Krulevitch et al. | |
| 8,596,859 B2 | 12/2013 | Wang et al. | |
| 8,674,656 B2 | 3/2014 | Iio et al. | |
| 8,784,381 B2 | 7/2014 | Watanabe et al. | |
| 8,807,131 B1 | 8/2014 | Tunnell et al. | |
| 9,022,988 B1 * | 5/2015 | Shaban ............. | A61M 5/31545 604/189 |
| 2003/0120217 A1 | 6/2003 | Abergel | |
| 2005/0174430 A1 | 8/2005 | Anderson | |
| 2008/0059133 A1 | 3/2008 | Edwards et al. | |
| 2010/0094455 A1 | 4/2010 | Dehlin et al. | |
| 2011/0253139 A1 | 10/2011 | Guthrie et al. | |
| 2012/0295240 A1 | 11/2012 | Walker et al. | |
| 2014/0193788 A1 | 7/2014 | Groves et al. | |
| 2014/0322682 A1 | 10/2014 | Baym et al. | |
| 2014/0350525 A1 | 11/2014 | Robinson et al. | |
| 2015/0051538 A1 | 2/2015 | Hata et al. | |
| 2015/0094689 A1 | 4/2015 | Steffen | |
| 2015/0290394 A1 | 10/2015 | Murakami et al. | |
| 2018/0304018 A1 | 10/2018 | Blondino et al. | |

FOREIGN PATENT DOCUMENTS

| | | |
|---|---|---|
| CN | 102245257 | 11/2011 |
| CN | 102300597 | 12/2011 |
| CN | 102413759 | 4/2012 |
| CN | 102614565 | 8/2012 |
| CN | 102099071 | 8/2013 |
| CN | 102202703 | 8/2014 |
| DE | 10057616 | 5/2002 |
| EP | 2541532 | 1/2013 |
| JP | H02-126858 | 5/1990 |
| JP | H03-139688 | 6/1991 |
| JP | 2010-178814 | 8/2010 |
| JP | 2011502630 | 1/2011 |
| JP | 2015-100096 | 5/2015 |
| RU | 2192285 | 11/2002 |
| RU | 2192894 | 11/2002 |
| RU | 2405574 | 12/2010 |
| RU | 138718 | 3/2014 |
| SU | 1286264 | 1/1987 |
| SU | 1651316 | 5/1991 |
| WO | WO 2009/141005 | 11/2009 |
| WO | WO 2010/021953 | 2/2010 |
| WO | WO 2011/139198 | 11/2011 |
| WO | WO 2013/069305 | 5/2013 |
| WO | WO 2014/080636 | 5/2014 |
| WO | WO 2016/203058 | 12/2016 |
| WO | WO 2016/203059 | 12/2016 |
| WO | WO 2016/204795 | 12/2016 |
| WO | WO 2016/207119 | 12/2016 |

OTHER PUBLICATIONS

International Search Report dated Aug. 24, 2016; International Application No. PCT/EP2016/064227.
International Search Report dated Aug. 26, 2016; International Application No. PCT/EP2016/064228.
International Search Report dated Aug. 26, 2016; International Application No. PCT/EP2016/064229.

* cited by examiner

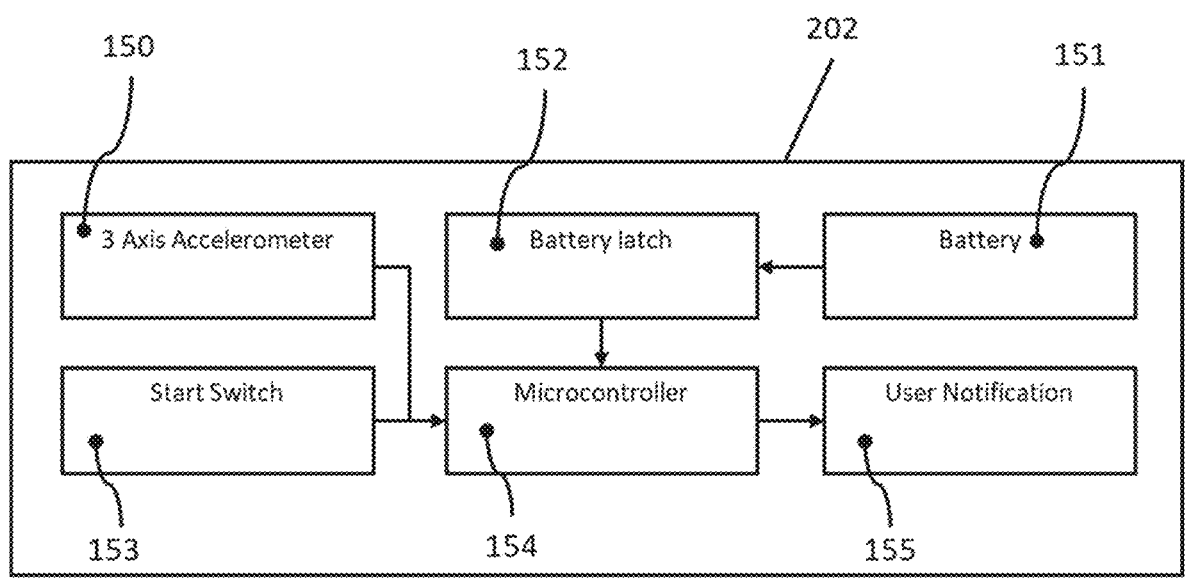
Figure 1A

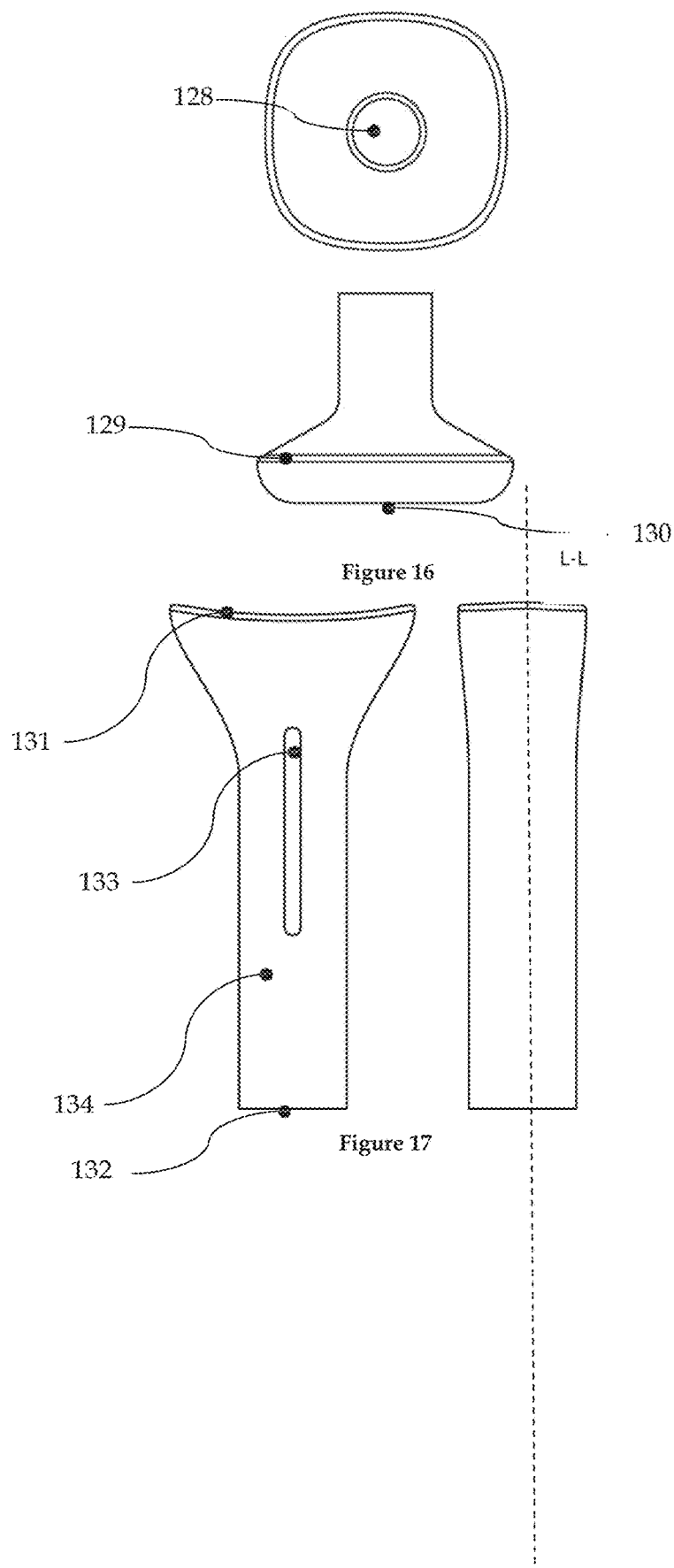

DEVICES AND METHODS FOR DRUG ADMINISTRATION AND MIXING, AND TRAINING OF PROPER TECHNIQUES THEREFOR

CROSS REFERENCE TO RELATED APPLICATIONS

This application is a continuation of U.S. application Ser. No. 15/736,362 filed on Dec. 14, 2017, which is a national stage of PCT Application No. PCT/EP2016/064229, filed Jun. 20, 2016, which claims priority to U.S. Application No. 62/182,426 filed on Jun. 19, 2015, the entire disclosures of which are hereby incorporated by reference in their entirety.

BACKGROUND

Pharmaceutical products intended for delivery by injection may be stored in vials or pre-filled syringes. In either case, when such products consist of two or more liquid and/or solid phases, they must be agitated prior to administration for optimum result, usually by manual shaking. Health Care Professionals (HCPs) and in some cases patients or caregivers, may not provide consistent agitation for a number of reasons. They may not be familiar with the pharmaceutical product; they may have habituated experience of similar pharmaceutical products which they presume to have the same or similar preparation steps; or they may mis-time the shake duration or required shaking vigor, mistakenly underestimating the time or vigor required to properly agitate the device and adequately mix the product.

SUMMARY OF THE DISCLOSURE

It is an aim of the present disclosure to provide a device that would provide the HCP with the knowledge and experience of the minimum duration and vigor of shaking required for the preparation of various pharmaceutical products such as, for example, INVEGA TRINZA™, which consists of particles in a suspension. It is also an aim to provide another device that alerts the user, for example when too much time has expired after mixing and the mixing step must be repeated. It is also an aim to disclose yet another device only works with the specified syringe for a particular product, and not, for example, a competitor syringe. This ensures that people do not mistakenly use the device with the wrong drug product, and can also be used as a means for differentiating one product relative to a competitor.

Accordingly, various embodiments of devices and methods to operate such devices to fulfill the needs and/or mitigate the shortcomings are disclosed. The present invention is defined by the appendant claims.

For example, in one aspect of the invention, a device is provided for training users how to properly mix pharmaceutical components. In another aspect, a device is provided for mixing pharmaceutical components, and assisting with the administration of properly mixed pharmaceutical components. In another aspect, a device for mixing and administrating properly mixed pharmaceutical components is disclosed. In another aspect, a device for attachment to a pharmaceutical delivery device and for assisting with the administration of properly mixed pharmaceutical components is disclosed. All of these devices are referenced herein (in both the description and claims) as the "device". The device may include a housing, for example a housing which extends along a longitudinal axis, for example with a power source disposed in the housing. A microcontroller may also be disposed in the housing and electrically powered by the power source as well as a user notification device and a motion or orientation detection device ("motion/orientation detection device), e.g. an accelerometer, disposed in the housing and electrically connected to the microcontroller. In this device, the microcontroller is configured to detect a motion and/or orientation of the housing and indicate via the user notification device as to whether the motion and/or orientation of the housing (e.g. when being shaken) during one of a drug administration or a training event is sufficient with respect to predetermined thresholds including magnitude of the force applied during shaking, acceleration of the housing during shaking, the orientation of the housing and/or duration of shaking.

Another aspect of the invention includes a method of operating such a device. The method can be achieved by determining from the motion/orientation detection device, e.g. accelerometer, if the magnitude of the motion and/or orientation of the housing are sufficient with respect to predetermined thresholds including magnitude of the force applied during the shaking, acceleration, the orientation of the housing and duration of such shaking; and announcing via the user notification device as to whether the motion or orientation of the housing being shaken during one of a drug administration or a training event meets the predetermined thresholds.

In addition to the various aspects described above, other features recited below can be utilized in conjunction therewith to arrive at different permutations of the invention. For example, the device may include a start switch electrically connected to the microcontroller; the accelerometer may include a 3-axis accelerometer; the accelerometer is configured to activate the microcontroller upon detection of movements of the housing during one of a drug administration or a training event; the microcontroller is configured to detect when shaking of the housing has ended prematurely, or if the level of shaking vigor has reduced to a level below the pre-set threshold, to enter a pause mode to allow the user to restart the shaking during one of a drug administration or a training event; the microcontroller is configured to set a timer and determine when a maximum allowable time after shaking of the housing has elapsed to warn the user to shake the device again during one of a drug administration or a training event; the housing may include a syringe barrel element with finger flange and one end and a barrel tip spaced apart along the longitudinal axis; the housing may include a body with a slot sized to accept a syringe barrel; the housing may include a housing provided with a compartment and a lid to receive an entire syringe; the housing may include an elongated body approximately the same length as a syringe barrel such that a syringe is inserted into a syringe receiving hole in the body and retained by the compressive force applied by the finger-like members between a syringe finger flange and a body base; the housing may include a body with a syringe accepting slot sized to accept a syringe barrel; the housing may include a puck-like body with a syringe accepting hole so that in use a syringe is inserted into the syringe accepting hole and is held in place with a user's thumb on an underside thumb grip.

These and other embodiments, features and advantages will be understood by those skilled in the art when taken with reference to the following more detailed description of the exemplary embodiments of the invention in conjunction with the accompanying drawings that are first briefly described.

BRIEF DESCRIPTION OF THE FIGURES

The foregoing and other features and advantages of the invention will be understood from the following, more particular description of preferred embodiments of the invention, as illustrated in the accompanying drawings.

FIG. 1A is a block diagram schematic of the electronic system/device of the present disclosure;

FIG. 16 illustrates a syringe puck embodiment, without syringe

FIG. 17 illustrates a trainer evoke embodiment;

Figure 1B:
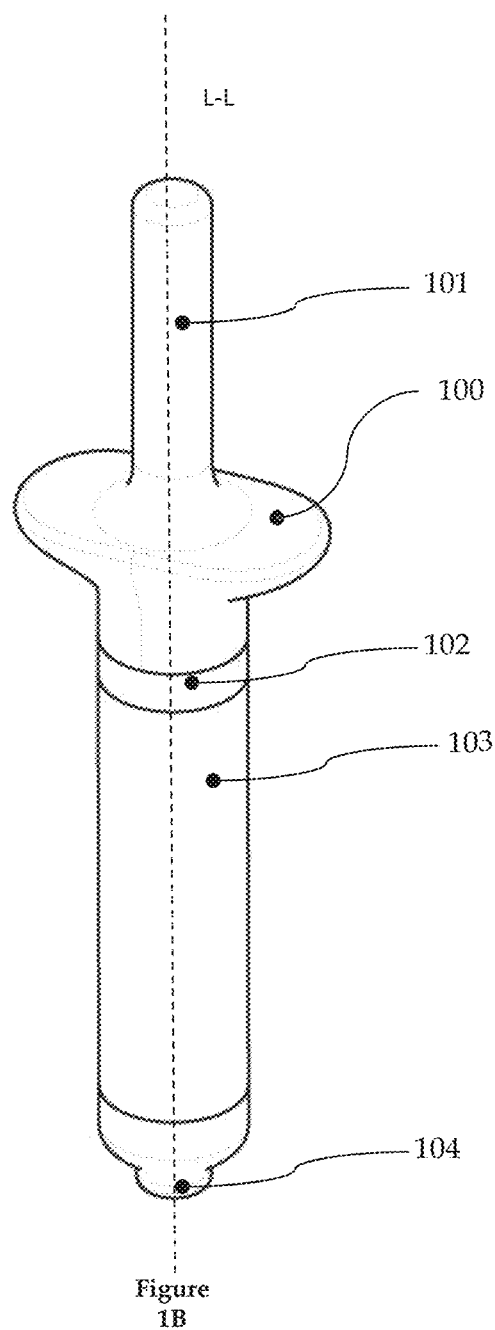
FIG. 1B illustrates a standalone mimic trainer embodiment, general view.

The accompanying drawings, which are incorporated herein and constitute part of this specification, illustrate presently preferred embodiments of the invention, and, together with the general description given above and the detailed description given below, serve to explain features of the invention (wherein like numerals represent like elements).

LIST OF REFERENCES

The following is a list of reference numerals relied upon in the figures:

100 Mimic trainer embodiment, plunger replacement
101 Finger flange
102 Light emitting feedback window
103 Barrel
104 Barrel tip
105 Syringe plunger rod
106 Syringe back stop
107 Syringe Barrel
108 Rubber stopper
109 Barrel attach embodiment body
110 Light emitting feedback window
111 Syringe clamping slot
112 Syringe retaining spring clip
113 Case lid
114 Case body
115 Case liner
116 Case hinge
117 Syringe
118 Springe clip
119 Light emitting panel
120 Lid catch
121 Elongated body
122 Light emitting band
123 Syringe receiving hole
124 Base of body
125 Syringe accepting slot
126 Light panel
127 Body
128 Syringe accepting hole
129 Light emitting band
130 Thumb grip
131 Finger grip
132 Thumb grip
133 Light emitting window
134 Body
135 Body
136 Blister tray packaging
137 Syringe
138 Side interference clips
139 Syringe slot
140 Light emitting band
141 Device attached to blister tray
142 Blister tray
143 Blister tray film
144 Syringe
145 Return clips
146 Light emitting strip
147 Device Body
148 Case base
149 Case top
150 3 Axis Accelerometer
151 Battery
152 Battery latch
153 Start switch
154 Microcontroller
155 User notification
200 Device
202 Housing
301 LCD 302 First state
303 Second state
304 Third state
305 Final state
401 Step: User applies shaking motion
402 Step: Detect motion and/or orientation
403 Step: Compare magnitude of motion and/or orientation with one or more thresholds
404 Step: Does motion and/or orientation meet the threshold(s)? Yes/No
405 Step: Notify user that motion and/or orientation meets the threshold(s)
406 Step: Notify user that motion and/or orientation does not meet the threshold(s)

DETAILED DISCLOSURE

The following detailed disclosure should be read with reference to the drawings, in which like elements in different drawings are identically numbered. The drawings, which are not necessarily to scale, depict selected embodiments and are not intended to limit the scope of the invention. This detailed disclosure illustrates by way of example, not by way of limitation, the principles of the invention. This disclosure clearly enables one skilled in the art to make and use the invention, and describes several embodiments, adaptations, variations, alternatives and uses of the invention, including what is presently believed to be the best mode of carrying out the invention.

As used herein, the terms "about", "approximately", or "substantially" for any numerical values or ranges indicate a suitable dimensional tolerance that allows the part or collection of components to function for its intended purpose as described herein. More specifically, "about", "approximately", or "substantially" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human, animal or medical use, although use of the subject invention in a human patient represents a preferred embodiment. Reference to "g" in terms of acceleration means 9.81 ms$^{-2}$, approximately 10 ms$^{-2}$.

The exemplary embodiments shown and described here may utilize an electronic system such as an electronic circuit mounted on a printed circuit board (PCB), which may include means to supply and control electrical power, means to measure spatial acceleration, means to time the duration of shaking and means to communicate the device state to the user as shown in FIG. 1A.

FIG. 1A shows components of a device 200 for training or aiding users in a proper mixing of pharmaceutical components. The device includes a housing 202, a microcontroller 154 disposed in or on the housing 202 and an accelerometer 150 disposed in or on the housing 202 and electrically connected to the microcontroller 154 so that the microcontroller 154 is configured to detect a motion and/or orientation of the housing 202. The microcontroller 154 may be disposed in the housing 202, such that it is contained by the housing 202. Alternatively the microcontroller 154 may be disposed on the housing 202 such that it is attached to the housing 202. Similarly the accelerometer 150 may be disposed in the housing 202 such that it is contained by the housing 202, or alternatively the accelerometer 150 may be disposed on the housing 202. Motion of the housing 202 may include shaking of the housing 202 by a user. Shaking may include reciprocating motion of the housing 202 for example in an up and down direction, or in a side to side reciprocating motion, or a combination of both, relative to the ground. Orientation of the housing 202 may be measured with reference to an approximately 1 g acceleration in the direction of gravity. The orientation may also be determined based on the integration of acceleration forces experienced by the accelerometer 150 with respect to time.

Referring still to the embodiment of FIG. 1A, the device 200 comprises a power source 151 disposed in the housing 202 and electrically connected to the microcontroller 154. The power source 151 may be disposed or contained in the housing 202 and may for example comprise a battery 151 or any other suitable power source, such as a capacitor. The power source 151 may be connected to the microcontroller 154 in order to power the microcontroller 154. It will be appreciated that various types of power source may be provided.

Specifically, the microcontroller 154 may be powered by the power source 151. The microcontroller 154 may optionally be powered by the power source 151, e.g. battery. This may be useful whilst the device 200 is in transit or if the device 200 is not to be used for a prolonged period of time.

The microcontroller 154 may be configured to detect low remaining power availability of the power source 151. In this case the microcontroller 154 can detect when the power source 151 is insufficient to achieve all the functions of the device 200, or if the power source 151 will be insufficient in the near future, e.g. to power the microcontroller 154 or accelerometer 150 such that they can function as intended or in the usual manner. This can be done by monitoring the voltage supplied by the power source 151, how the voltage varies under different loads, what power is available, or how stable the supply is. If a rechargeable battery is used, then the microcontroller 154 may additionally be able to monitor the health of the battery.

Still referring to the embodiment of FIG. 1A, the microcontroller 154 may be configured to detect an error or fault in the functioning of the device 200. For example, the fault may be in one or more of the motion/orientation device 150, the housing 202 or its attachment to or containment of a pharmaceutical delivery device. As an example, in the case of an accelerometer 150 or any other motion/orientation device, the microcontroller 154 may receive an unexpected signal, or it may receive no signal at all. If this is detected by the microcontroller 154, the unexpected signal or lack of signal may be detected as an error in the device 200. Similarly, the microcontroller 154 may be able to detect the state of the housing 202 or of a contained pharmaceutical delivery device, e.g. whether the housing 202 is closed and/or the delivery device is properly or sufficiently inserted into the housing 202. Similarly the microcontroller 154 may be able to detect an unexpected signal or no signal, e.g. from the microcontroller 154 or accelerometer 150, when there should be and register this as an error or fault.

In a device 200, as described above, in which the microcontroller 154 detects a low remaining power availability of the power source 151 or when the microcontroller 154 detects the fault or error, it may perform one or more of: issuing an alert representative of the low remaining power availability to the user (for example via the user notification device 155), and/or preventing activation of the pharmaceutical delivery device for delivery of the pharmaceutical components to a user. The device 200 may issue an alert to the user that there is a low power availability. This allows the user to take rectifying action, or to know that the device 200 may not be usable now or in the future. If the power drops to a certain point it is possible that the circuit, the microcontroller 154, or any other components may become unreliable. For example, an unstable power supply to a microcontroller 154 could lead to unexpected results from the microcontroller 154. If this is the case, then it is possible that the device 200 could encourage incorrect behavior of the user, such as not requiring the completion of a shaking event or not correctly detecting a threshold. This could lead to use of pharmaceutical components which are not properly mixed. In this case, the microcontroller 154 may prevent activation of the pharmaceutical delivery device for the delivery of pharmaceutical components to a user. Prevention of activation of the delivery device may be achieved in a number of ways. Wherein the shaking device 200 is also the drug delivery device, the microcontroller 154 may be connected to an activatable lock which acts against the delivery device deliver mechanism or activator to prevent expulsion of the pharmaceutical components, e.g. via a stop which can be moved into a locked position from an unlocked position and vice-a-versa. The lock may be a device which obstructs the flow of the pharmaceutical components out of the device through a nozzle, such as a valve. Alternatively, in the case where the drug delivery device comprises an actuator for actuating the delivery of the pharmaceutical components, the lock may be a component which obstructs the actuator from expelling the components. In the case where an actuator is driven automatically by a spring, the lock may also be a component which disengages the spring from the actuator, such that it cannot expel the components from the drug delivery device. In the case where the shaker device of the present invention engages with a separate drug delivery device, such as clipping on or containing the device, then the shaker device may prevent activation of the drug delivery device by other means. In one example, the drug delivery device comprises a circuit which may communicate with the microcontroller 154 of the shaker device. Communication may be achieved by electrical connection when the two devices are connected, or alternatively by wireless communication. The circuit of the drug delivery device may be active or it may be passive, it may also comprise its own power source, or share the power source 151 of the shaker device. In this aspect the drug delivery device may achieve prevention of activation of the pharmaceutical delivery device by the same means as described above. Alternatively, the shaker device may comprise an actuatable lock which interacts with a corresponding lock on the drug delivery device. The actuatable lock of the shaker device 200 may mechanically couple with a corresponding lock on the drug delivery device to prevent actuation of the drug delivery device. Alternatively, the actuatable lock of the shaker device 200 may be a moveable magnet. When the drug delivery device is engaged with the shaker device 200 the moveable magnet may be moveable between a first position, in which the delivery device may not be activated, and a second position in which the delivery device may be activated. For example, in order to prevent activation of the delivery device, the moveable magnet may be moved such that a magnetic ball in the delivery device obstructs the expulsion of the pharmaceutical components. Alternatively to a moveable magnet, the shaker device 200 may comprise an electromagnet which may be activated or deactivated to provide a moving magnetic field which may selectively prevent activation of the delivery device.

The device 200 may comprise a delivery device identification unit in communication with the microcontroller 154. In this case the device 200 may have means of identifying delivery devices. The device 200 may be capable of reading an RFID tag, a barcode, or text on the delivery device. In this case the device 200 may be capable of detecting if the correct delivery device is being used. The delivery device identification unit may be configured to read data on data storage means of a delivery device contained in use in the housing 202, wherein the read data is characteristic of the pharmaceutical components contained in the device 200 and/or delivery device itself. In this case, the microcontroller 154 may identify the pharmaceutical components in the delivery device. The data may comprise one of more of: an expiration date of the pharmaceutical components, whereby the microcontroller 154 is configured to alert a user via a user notification device 155 of the device 200 if the current date as determined by the microcontroller 154 exceeds the expiration date, and/or data identifying the pharmaceutical components contained within the delivery device, for example data indicative of manufacturer or composition of the pharmaceutical components, whereby the microcontroller 154 is configured to alert a user via a user notification device 155 of the device 200 if the data identifying the pharmaceutical components does not match or sufficiently correspond to permitted pharmaceutical components as stored in the microcontroller 154 or in memory connected thereto. The microcontroller 154 may include a clock which keeps track of the current date and/or time, or the microcontroller 154 may be configured to receive the current date and/or time from an external source, such as a radio signal. In either case the current date may be compared with an expiration date of the pharmaceutical components. The data read from the storage means may include the specific expiration date, or information which allows the expiration date to be calculated. For example, the data read from the storage may include a production date and an indication of how long the pharmaceutical components may be stored. The data may include data identifying the components themselves. This data may be a name of a component which may or may not be encoded. The encoded name of the components may then be correlated to the actual components. The data identifying the pharmaceutical components may also be used to identify the correct level of vigor and/or time for shaking for mixing the components prior to shaking. The user notification device 155 may indicate to the user instructions for properly mixing the pharmaceutical components. The microcontroller 154 may further alert the user if the data identifying the components does not match or sufficiently correspond to permitted pharmaceutical components. Advantageously this alerts the user in cases where the incorrect pharmaceutical components are about to be used. The correct components to use may be stored in the microcontroller 154 or memory prior to the use of the device 200.

The above-mentioned data may comprise one or more of: the expiration date of the pharmaceutical components, whereby the microcontroller 154 is configured to prevent activation of the pharmaceutical delivery device for delivery of the pharmaceutical components to a user if the current date as determined by the microcontroller 154 exceeds the expiration date, and/or data identifying the pharmaceutical components contained within the delivery device, for example data indicative of manufacturer or composition of the pharmaceutical components, whereby the microcontroller 154 is configured to prevent activation of the pharmaceutical delivery device for delivery of the pharmaceutical components to a user if the data identifying the pharmaceutical components does not match or sufficiently correspond to permitted pharmaceutical components as stored in the microcontroller 154 or in memory connected thereto. In these examples, the microcontroller 154 is capable of preventing use of the delivery device in the cases where the pharmaceutical components have expired or are not those intended for use. This may be achieved via the mechanism described above.

As shown in FIG. 1B, which shows one specific embodiment of this disclosure, the housing 202 may extend along a longitudinal axis L-L. The housing 202 may be elongated such that it mimics or is a suitable shape for supporting a container for pharmaceutical components.

The housing 202 comprises a major longitudinal axis L-L. Drug delivery devices may be elongated or have a major longitudinal axis, as for example shown in FIG. 1B. Such a device 200 may also be elongated or have a major longitudinal axis. This may be to mimic or contain a drug delivery device or other container for pharmaceutical components, for example a vial.

Figure 3:
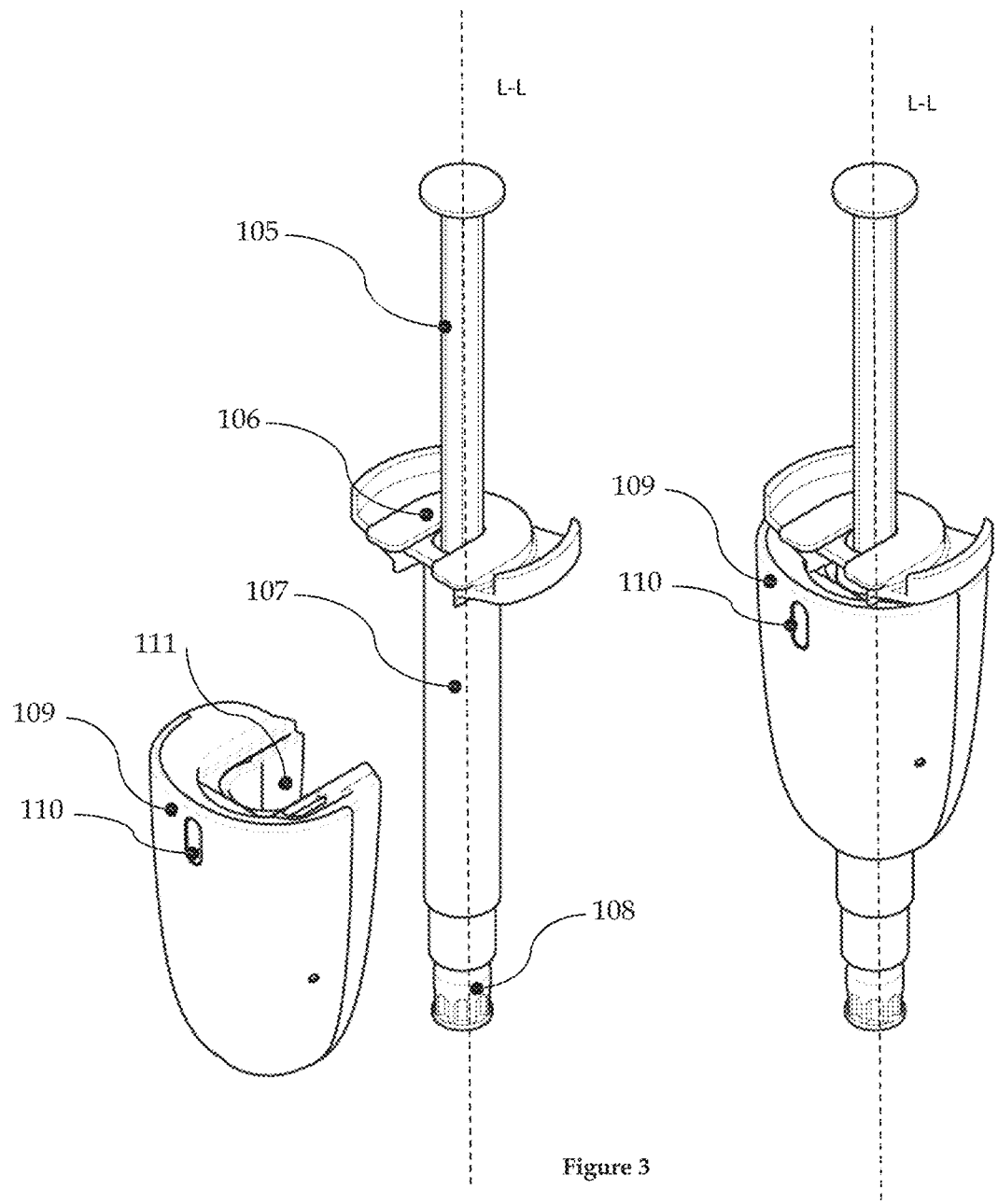
FIG. 3 illustrates a syringe barrel attachment embodiment, showing device separate from, and attached to syringe.

The housing 202 may be adapted to receive a drug delivery device having a major longitudinal axis, and to further align its major longitudinal axis along the major longitudinal axis of the drug delivery device, as for example shown in FIG. 3. Advantageously, such a device 200 may allow the drug delivery device to be received in a particular orientation. Since the axes of the device 200 and of the drug delivery device are aligned, the alignment of the drug delivery device with respect to any other components which may be fixed to the housing 202 is known. If, for example, the orientation of the microcontroller 154 is known with respect to the housing 202, and the major longitudinal axes of the two devices are aligned, then the orientation of the microcontroller 154 with respect to the drug delivery device is known.

The microcontroller 154 may be configured to detect a motion and/or orientation of the housing 202 with respect to motion along or about the longitudinal axis, in which case the accelerometer 150 is able to distinguish between acceleration forces along the longitudinal axis of the housing 202 and acceleration forces about the longitudinal axis. An axis of an accelerometer 150 may be aligned with the longitudinal axis of the housing 202 such that measurements by that axis correspond to motion along the longitudinal axis of the housing 202. Alternatively the accelerometer 150 may have at least two axes which are not aligned with the longitudinal axis of the housing 202 and the forces may be resolved in order to determine the motion along the longitudinal axis. The accelerometer 150 may also detect motion in any other direction, or rotation about any other axis. The accelerometer 150 may also detect the orientation of the housing 202 with respect to the motion which is being applied to it. The method of operation of the device 200 as controlled by the microcontroller 154, e.g. via executable instructions executing therein, is shown in FIG. 28.

Figure 28:
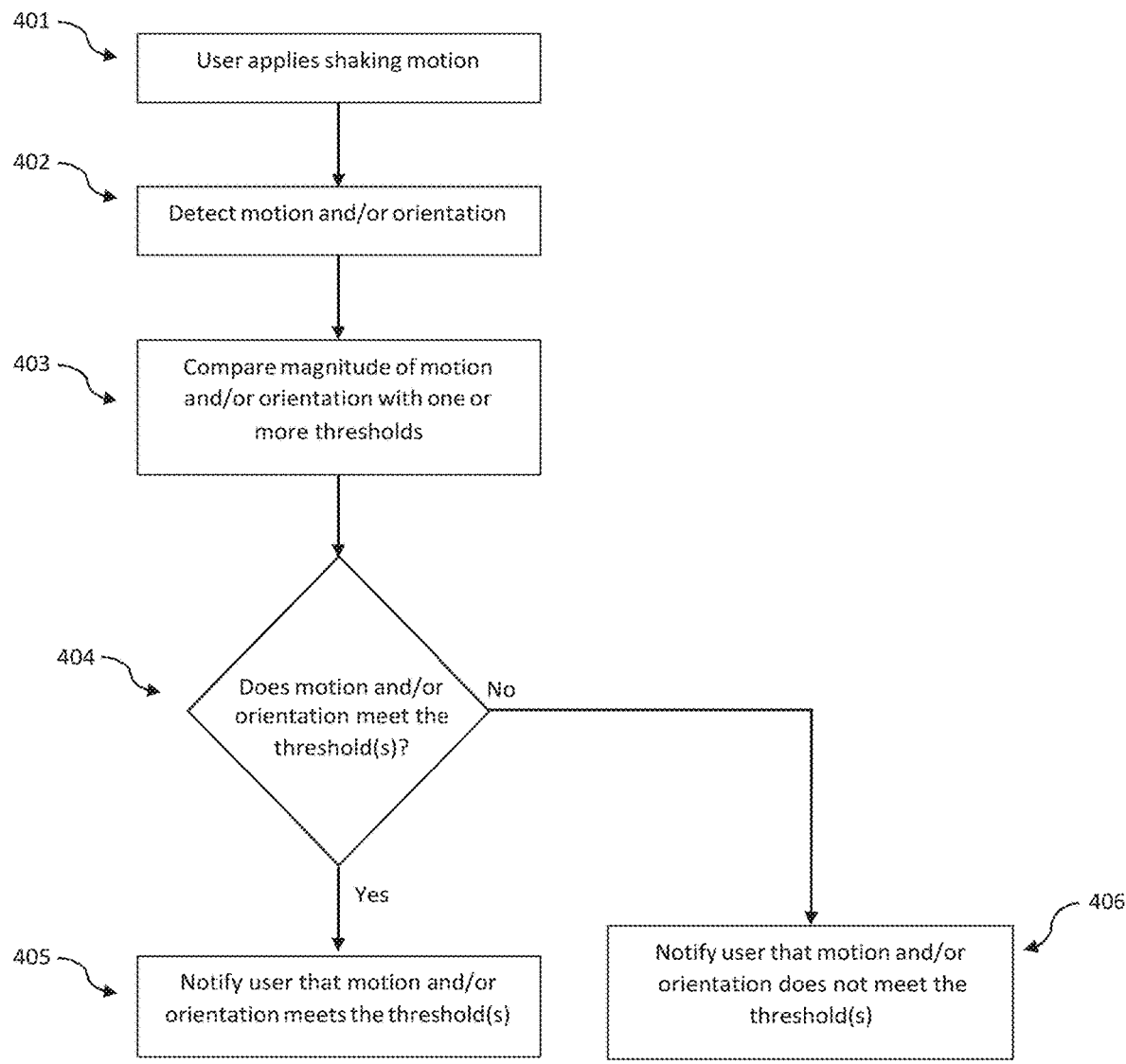
FIG. 28 is diagram showing a method of operation of the implemented system/device of the present disclosure.

With reference now to FIG. 28, in a shaking event a user applies 401 a shaking motion to the device. The device detects 402 the motion and/or the orientation of the device. The device compares 403 the magnitude of the motion and/or the orientation of the device with respect to one or more thresholds. At 404 if the motion and/or orientation of the device meets the threshold or thresholds then the process moves to notify 405 the user that the motion and/or orientation meets the threshold or thresholds. At 404, if the motion and/or orientation of the device does not meet the threshold or thresholds then the process moves to notify 406 the user that the motion and/or orientation does not meet the threshold or thresholds.

As shown in FIG. 1A the device 200 may include a user notification device 155 in communication with the microcontroller 154. The user notification device 155 may provide user notifications as instructed by the microcontroller 154. The user notification device 155 may comprise one or more of: a display, a tactile feedback unit, a light emitting device and/or a vibratory alert unit. The user notifications may include one or many of a notification that the device 200 is on, the device 200 is off, shaking has commenced, shaking has paused, shaking has stopped, the wrong frequency of shaking is being applied, the correct frequency is being applied, sufficient shaking has taken place, or too much time has elapsed post completed shaking. The user notification device 155 may indicate notifications to the user by visual means such as a light emitting component or an LCD screen. For example an LCD display comprising a number of pixels or other elements may be used. The display may be of a type which reflects light, a type which transmits a backlight, or a type which emits light. A light emitting device may include a light emitting diode. The light emitting diode may be configured to emit light of one particular colour, or of a number of colours. The light emitting device may also comprise a light bulb. Optionally the user notification device 155 may indicate to the user by audible means, such as a buzzer or a speaker. Optionally the user notification device 155 may be tactile by means of vibration or the physical movement of a component by motor. Beneficially, the user feedback allows the user to modify his or her behavior in response to feedback from the device 200. In one example, in use, if the user begins shaking the device 200 at a suitable level of vigor but then ceases to sustain the sufficient level of vigor as measured by the accelerometer 150, the device will notify the user to apply more vigor. This could be by an audible alarm, a visual cue or by tactile vibration. Alternatively the device 200 can provide a positive feedback whilst attaining a sufficient level of vigor and then removing the feedback when the user drops below this. For example, tactile feedback can confirm that the shaking is sufficient which will cease when the user no longer attains this level. Alternatively a light may be on when the user is shaking sufficiently and may turn off when the level of shaking is insufficient. The user notification device 155 may be mounted on an external surface of the housing 202 for notifying the user as to its status. This may be particularly useful in the case of user notification devices providing visual feedback since this places them in a position where they be more easily seen by the user. Although any user notification device may benefit from being positioned in this manner, in closer proximity to the user.

In the case of the user notification device 155 being a display, the microcontroller 154 may be configured to indicate via the display a state of mixing or simulated mixing of the pharmaceutical components in a real-time manner. In this way the user is provided with feedback which allows the user to understand how far through the shaking event they have progressed. This may be an indication of how much time the user has been shaking under satisfactory conditions. This may also be an indication of how well the components have or would have been mixed. For example, shaking at a higher intensity may promote mixing of the components, in which case the display may be configured to indicate that the mixing has progressed further after the same duration of shaking at a lower intensity. As a further indication the microcontroller 154 may be configured to change progressively the colour and/or pattern of one or more display elements on the display as shaking takes place until sufficient shaking has taken place for satisfactory mixing or satisfactory simulated mixing of the pharmaceutical components for delivery. This allows the user to be made aware of the progression of the shaking event or of the mixing of the pharmaceutical components by means of changing the colour of one or more display elements. For example a display element may change from red to green, from green to red, or indeed any other change in colour, to indicate that the mixing has progressed. The display may also change the pattern of the display elements. For example this could be a bar graph which progresses, or it may be an arrangement of display elements which indicate a more sparse arrangement as the mixing progresses. The display may also use any combination of these changes in the display elements to indicate to a user that satisfactory mixing or satisfactory simulated mixing is occurring.

Figure 26:
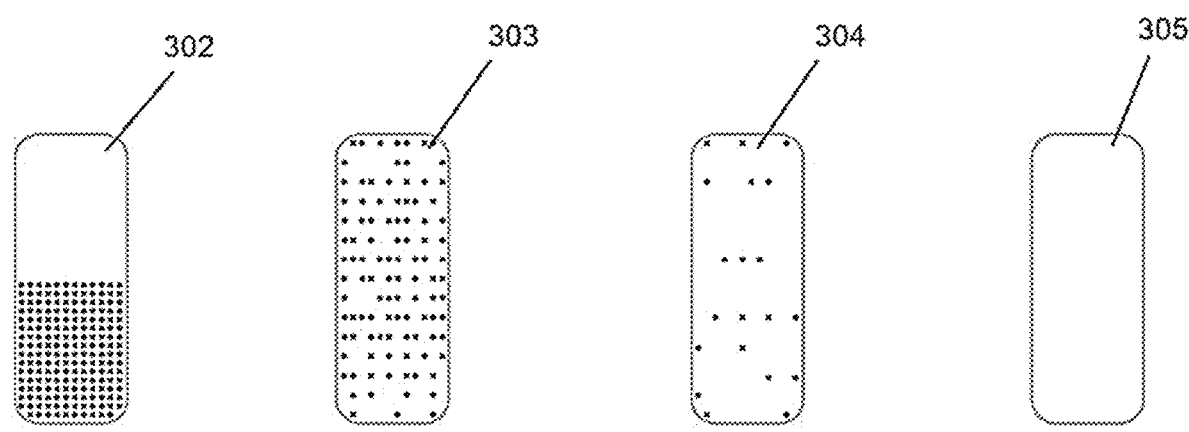
FIG. 26 illustrates LCD screen conditions showing stages of mix from sediment on left to mix on the right.

Furthermore, in the case where the device 200 includes a display 301, and with reference to FIG. 26, the microcontroller 154 may be configured to display at least two types of display elements on the display 301 which are grouped together in at least two discrete portions of the display 301 prior to commencement of shaking, and which progressively mix with each other on the display 301 so long as shaking continues at a sufficient enough or pre-defined force and/or for a sufficient enough or predefined duration, until such time that it is determined that sufficient shaking has taken place for satisfactory mixing or satisfactory simulated mixing of the pharmaceutical components for delivery, at which time the at least two types of display elements are wholly integrated with each other in a regular pattern across the display 301. In this way the user is provided with an intuitive display of the progress of the mixing. In a training event there may be no pharmaceutical components for the user to see. In this case the display 301 provides a visual feedback capable of representing how well mixed the components are. In the case of either a training event where the pharmaceutical components are present or an actual mixing event, the user may not be able to see the pharmaceutical components in situ or it may be difficult to see the degree of mixing due to the visual properties of the pharmaceutical components. In any case, the display 301 provides feedback to the user which can be easily identified as components mixing. There may also be more than two types of display element which may achieve a similar effect as the two types of display element.

In a device 200 in which there are only two types of pharmaceutical component to be mixed or simulated for mixing, and wherein there are only two types of display element, one of the types of display element may correspond to one of the pharmaceutical components and the other type of display element may correspond to the other one of types of display element. Corresponding display elements with pharmaceutical components in this way provides an intuitive display which represents a state of mixing to the user or a progression of the mixing event. This may be extended to other compositions which include more than two components wherein each component corresponds to a different type of display element. Further to this, two types of display element may be used to represent more than two pharmaceutical components. Alternatively, more than two types of display element may be used to represent two pharmaceutical components.

The microcontroller 154 may be configured to detect in a shaking event whether the motion and/or the orientation of the housing 202 being shaken during one of a pharmaceutical administration or a training event is sufficient with respect to one or more predetermined thresholds including one or more of: magnitude of the force applied to the device 200 during the shaking, orientation of the housing 202, acceleration of the device 200, and duration of such shaking. A number of factors may affect the efficacy of the shaking in achieving mixing of pharmaceutical components. For example, a user who shakes the device 200 "harder" may be causing a greater acceleration of the device 200 at either end of the swinging motion. This greater acceleration and harder shaking may cause faster mixing of the components as the forces which they experience will be greater, causing better dispersion. Although "harder" shaking may lead to better mixing, it is also possible that for a particular composition of pharmaceuticals the added benefit of "harder" shaking above a certain threshold may be diminishing. Hence, the device 200 may only require a certain threshold to be met and then record the shaking activity from that threshold. In some cases the orientation of the housing 202 may affect the mixing of the pharmaceutical components, in which case the device 200 will detect by the accelerometer 150 which direction the swinging action of the shaking is being applied in and provide feedback accordingly. For example, the user may be shaking the device 200 across the longitudinal axis instead of along it. In this case the device 200 may ignore this shaking motion since it does not benefit the mixing of the pharmaceuticals. Alternatively, it may be known that shaking across the longitudinal axis may still benefit mixing of the pharmaceuticals and the device 200 can then include this shaking in the monitoring of the shaking activity. Shaking of the device 200 across the longitudinal axis may contribute to the recording of the shaking activity to any of a lesser, the same, or even a greater degree than shaking along the longitudinal axis. In a further aspect, if the device 200 includes a user notification device 155, the microcontroller 154 may indicate to the user whether the motion or orientation of the housing 202 being shaken is sufficient with respect to one or more of the predetermined thresholds.

Applicable sufficient thresholds for mixing two pharmaceutical components may be in one of the following ranges: 2 g to 15 g, 5 g to 12 g, and 7 g to 10 g or at a threshold of 3 g, 4 g, 5 g, 6 g, 7 g, 8 g, 9 g or 9.3 g. Suitable orientation of motion along the longitudinal axis for mixing whilst may be substantially along the longitudinal axis, or vertically with respect to the ground, or in the range+/−2 degrees each side of the longitudinal axis, +/−2 degrees each side of the longitudinal axis, +/−10 degrees each side of the longitudinal axis, +/−20 degrees each side of the longitudinal axis, +/−30 degrees each side of the longitudinal axis. These thresholds may be suitable for mixing the components of INVEGA TRINZA™ as described in further detail below.

Referring again to FIG. 1A, the device 200 comprises a start device 153 in communication with the microcontroller 154. The start device 153 may be configured to commence detection for the shaking event by the microcontroller 154. Advantageously the start device 153 provides an input to the device 200 to indicate with precision when the device 200 is going to be used. This may allow the device 200 to conserve power since it may enter a low power mode, in which the microcontroller 154 and/or other components of the device 200 are configured to draw less power from a power source 151. The start device 153 may be one of a start switch in communication with the microcontroller 154, a start button in a user interface displayed by a touch sensitive display screen of the device, or the start device 153 may be a motion sensitive device which may indicate that detection of the shaking event should commence when the housing 202 is moved. The use of a start device 153 allows the user to choose when the device 200 may be prepared to detect the shaking event. This may be useful if, for example, the device 200 is to be carried around or shipped to another location and will help preserve the power source 151 for actual use rather than accidental triggering of the device 200.

Wherein the start device 153 is a start switch, the start switch may be configured to activate the microcontroller 154 from a power conservation mode into an active mode upon detection of the movement of the housing 202 during one of a drug mixing and administration event, or a training event. This allows the device 200 to conserve power when it is not in use or when it is not about to be used. The start switch 153 may be configured to activate the microcontroller 154 at one of a number of threshold levels of movement of the housing 202. For example, the start switch 153 may be configured such that a user picking up the device 200 activates the microcontroller 154. Alternatively the start switch 153 may be configured such that a user is required to give the device 200 a sharp impulse in order to activate the microcontroller 154. Alternatively the start switch 153 may be configured such that the user must shake the device 200 more than once in order to activate the microcontroller 154.

During such a power conservation mode the microcontroller 154 may be configured during the power conservation mode, to draw reduced power with respect to the active mode, or no power at all, from the power source 151. In this way the device 200 may conserve power when it is not being used. This advantageously saves the use of a power source 151 for when it is needed. In a case where the power source 151 is a battery, the battery charge may be conserved during periods of inactivity to prolong the lifetime of the battery in the device 200. Other power sources may also benefit from the conservation of their use.

Alternatively or additionally to a start switch, the accelerometer 150 may be configured to commence detection for the shaking event upon detection of movement of the housing 202 in excess of a predetermined level during one of a pharmaceutical administration or a training event. Beneficially in this aspect the user may simply start shaking the device 200 and the device 200 will begin recording the shaking automatically. Advantageously, such a device does not necessitate physical components such as switches or a touch screen on the outside of the device 200. This may allow the device 200 to either be free from external physical components or reduce the number of external physical components on the device 200. This can improve the usability of the device 200 or make it simpler to operate.

The microcontroller 154 may be configured to detect via the accelerometer 150 when shaking of the housing 202 has ended prematurely. The microcontroller 154 receives a signal from the accelerometer 150 and measures how long the shaking has occurred for. If the shaking ceases, the microcontroller 154 receives a signal from the accelerometer 150 which indicates that the shaking has stopped and the microcontroller 154 can compare the actual duration of shaking to the required time of shaking. The microcontroller 154 may also be configured to detect via the accelerometer 150 if the level of shaking vigor has reduced to a level below the one or more pre-set thresholds. Even if the user has not stopped shaking the device 200, the degree of shaking may not be enough to meet the requirements for mixing of the pharmaceutical components. In this case the microcontroller 154 is configured to detect that the force is not high enough to meet the threshold. The microcontroller 154 may also be configured to detect if the average level of shaking vigor over a predetermined time of the shaking event reduces to a level below one or more pre-defined thresholds. In this aspect a greater degree of flexibility by the shaking measurement is achieved. More than one threshold may be set in order to more accurately determine whether the correct degree of shaking has occurred. One threshold may be set that requires a lower intensity of shaking for a longer time, whilst another threshold may be for a higher intensity over a shorter time period, or vice versa. This allows the device 200 to determine more accurately how well the device 200 has been shaken. The microcontroller 154 may also be configured to detect via the accelerometer 150 if the component of shaking in a predetermined direction is insufficient with respect to a predetermined level. Advantageously in such a device, the microcontroller 154 is able to differentiate between shaking in a number of directions, either along the longitudinal axis or in any other direction. The microcontroller 154 may also be able to determine if a rotation in any direction is being applied to the device 200. The microcontroller 154 may give a certain weighting to the different components of the shaking action and/or may combine all of the readings in the different directions to determine whether a total degree of mixing has occurred.

The microcontroller 154 may be configured to notify a user of unsatisfactory shaking when one or more of the events is detected. Notification to the user may be achieved by means of the user notification device 155. This may be a positive feedback such as turn on or flashing a light such as an LED, a message displayed on a screen, a vibration as tactile feedback, a sound emitted from a sound emitting device, or alternatively a negative feedback such as removing the presence of any of these notifications.

The microcontroller 154 may be configured to notify a user of satisfactory shaking after or at a given time of passing of the shaking event, such that satisfactory shaking is indicated by one or more of the events not being detected. Notification may be given to the user by turning on or flashing an LED, changing the colour of an LED, displaying a message on a screen, giving tactile feedback such as vibration, emitting a sound from a speaker or a buzzer, or ceasing to provide any of these notifications as positive feedback. Further to this, the given time of passing may be at the completion of the shaking event such that the components are mixed or the simulated components are mixed.

The microcontroller 154 may be configured to enter a pause mode to pause detection by the microcontroller 154 and subsequently allow the user to restart shaking and continue detection during the shaking event. A user may need to stop shaking the device 200 momentarily so that their grip may be adjusted for example, or in order to rest for a short while. In any case the device 200 is configured so that a break in the shaking of a sufficiently short time does not mean that the shaking cannot be continued. If the user stops shaking to readjust his grip, he may then continue to shake the device 200 and the microcontroller 154 will exit the pause mode and continue to measure the elapsed time and shaking.

The microcontroller 154 may be configured to start a timer and determine when a maximum allowable time after shaking of the housing 202 has elapsed to warn the user via the user notification device 155 to shake the device 200 again during one of a drug administration or a training event. Following a mixing procedure of a pharmaceutical composition the components may begin to separate. After enough time has elapsed after mixing, the composition will no longer be in a state in which the user should be administering the composition any more, for example the suspension of particles may have formed a sediment. Advantageously, when using a device 200 in which the microcontroller 154 determines the maximum allowable time, the user is notified when too much time has elapsed and the device 200 should be shaken again before administration of the drug. In the case of a drug administration device or aid the user will be notified and will need to shake the device again to mix the components. In the case of a training event the user will be notified of the time after which the drug should have been administered and aids in training.

As shown in the embodiment of FIG. 1A, the accelerometer 150 may comprise a 3-axis accelerometer 150 which is configured to detect a component of shaking acceleration in each of three tangential directions and provide data indicative of the components to the microcontroller 154. Advantageously this device does not require the accelerometer 150 to be positioned in a certain orientation in the device 200 to be able to detect the longitudinal shaking of the device 200, or indeed any other direction of shaking. Furthermore, the microcontroller 154 may indicate to the user that shaking is not taking place in the correct direction to mix the pharmaceutical components. Further to this, the microcontroller 154 may also take into account shaking action in a number of directions and use each of them to determine whether the shaking event has been successful.

Figure 2:
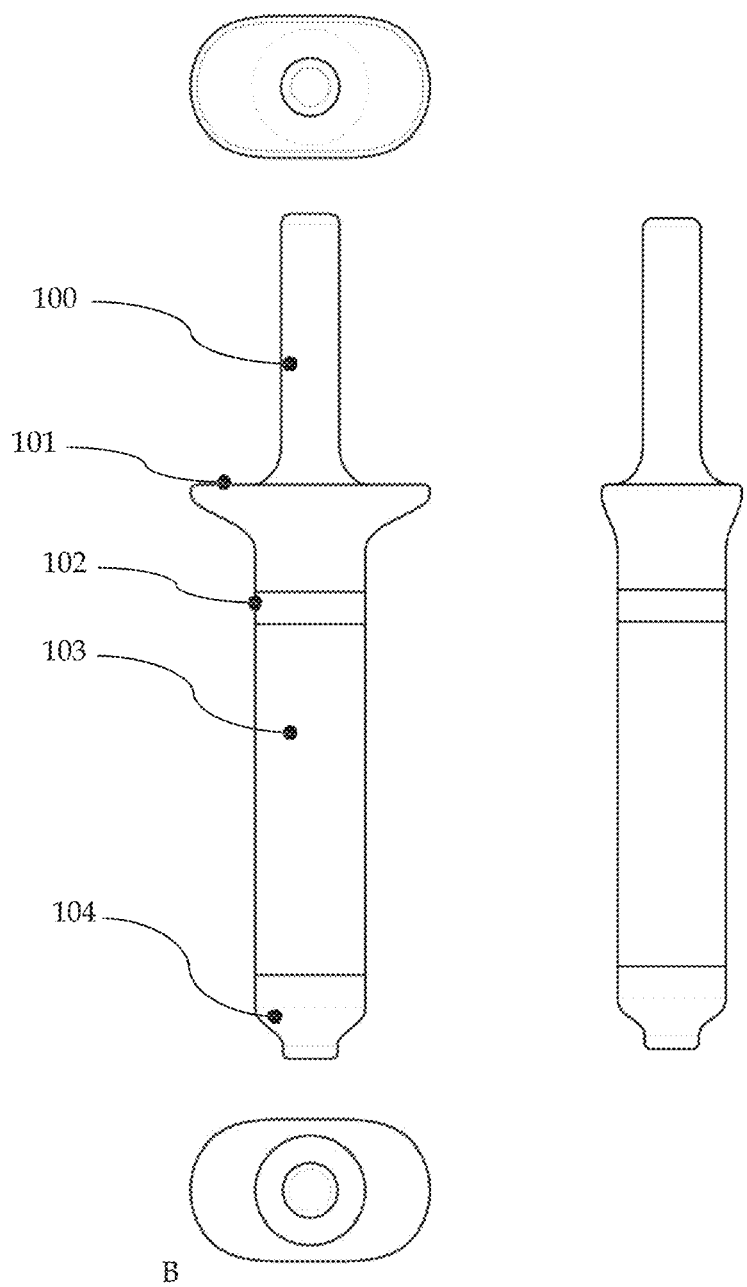
FIG. 2 illustrates a standalone mimic trainer embodiment, orthographic views.

With reference to the embodiments of FIGS. 1B and 2, the housing 202 comprises syringe-shaped components located on or formed by the housing 202. Advantageously, these components provide the components in a training device which mimic those present in an actual syringe. In this device the housing 202 provides tactile feedback to the user which is similar to that which would be experienced from use of an actual syringe and assists in the ability to train a user.

Specifically the syringe-shaped components may comprise a syringe-like barrel element 103 with finger flange 101 at one end and a barrel tip 104 spaced apart along the longitudinal axis. These components are mimetic of key features of a syringe which the user may experience handling for the purposes of mixing pharmaceutical components.

The housing 202 may be configured to receive a pharmaceutical delivery device containing the pharmaceutical components. The pharmaceutical delivery device may be a syringe which the user may actuate manually by depressing a plunger, or the delivery device may be an automatic injector. In any case the housing has a form which allows the delivery device to be at least partially received. Further examples are given in the rest of this disclosure.

With reference to FIG. 3, the housing 202 comprises a body 109 dimensioned and/or shaped to accept a syringe barrel 107 or a vial. The housing 202 cooperates with the syringe barrel 107 or vial so that the user is able to shake and mix the actual pharmaceutical components whilst still receiving the feedback from the device. Alternatively the device 200 may still be used to train the user in the proper technique before applying it to the actual pharmaceutical components prior to administration. When the device 200 is joined to the syringe barrel 107 or vial, it is able to measure the shaking of the syringe barrel 107 or vial by proxy.

Figure 6:
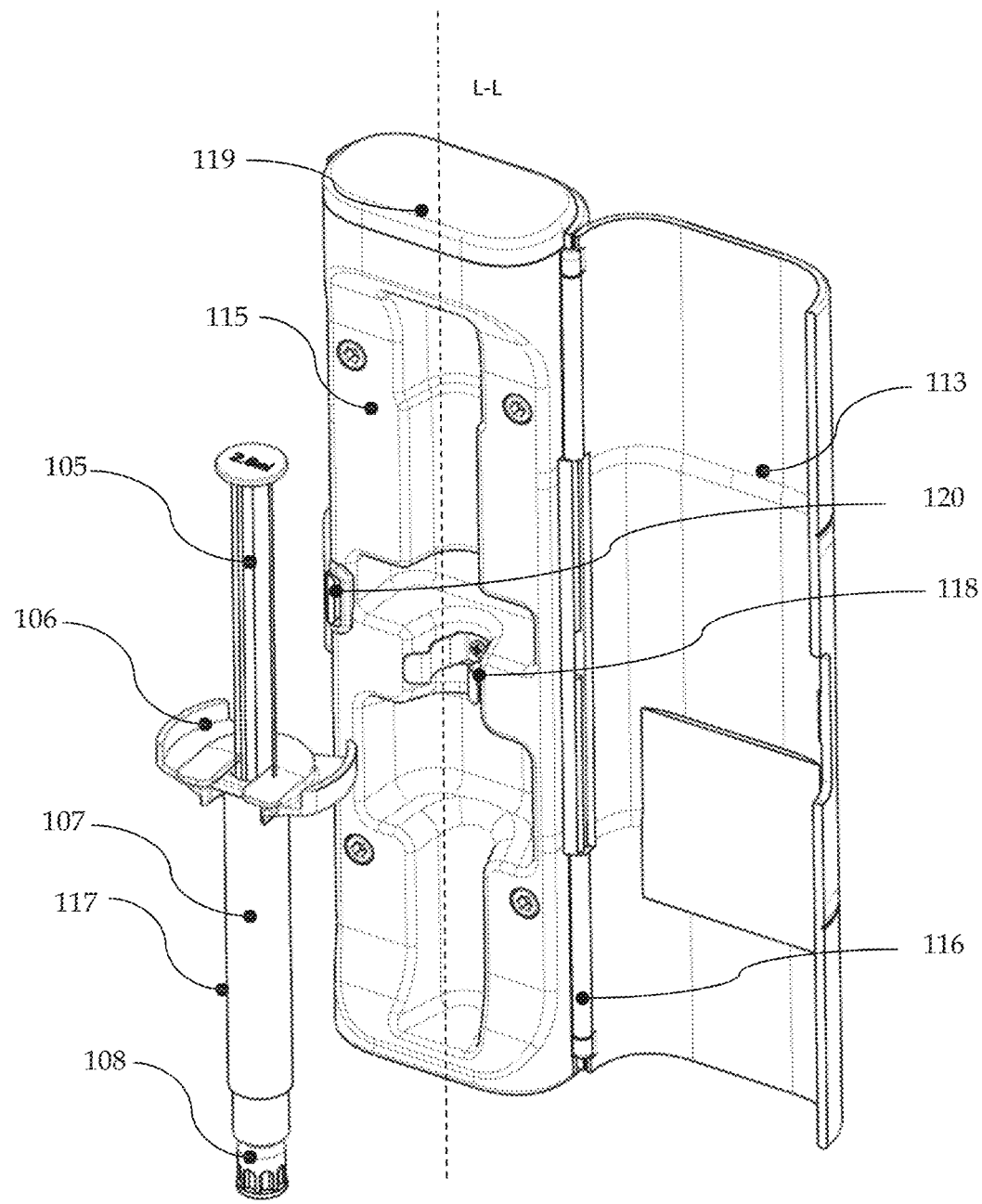
FIG. 6 illustrates a syringe case embodiment, general view showing syringe next to open case.

With reference to FIG. 6, the housing 202 comprises a compartment to receive an entire syringe 117 or an entire vial. In this case the device 200 may fully contain the syringe 117 or vial. This may aid users who find the size or form of the syringe 117 or vial difficult to hold. Alternatively or additionally this device 200 may provide a degree of protection to the syringe 117. Fully receiving the syringe 117 or vial may also disguise the syringe 117 or vial such that the contents may not be easily viewed by people other than the user. In cases where there may be a perceived social stigma in relation to syringes, this may benefit the user.

Figure 7:
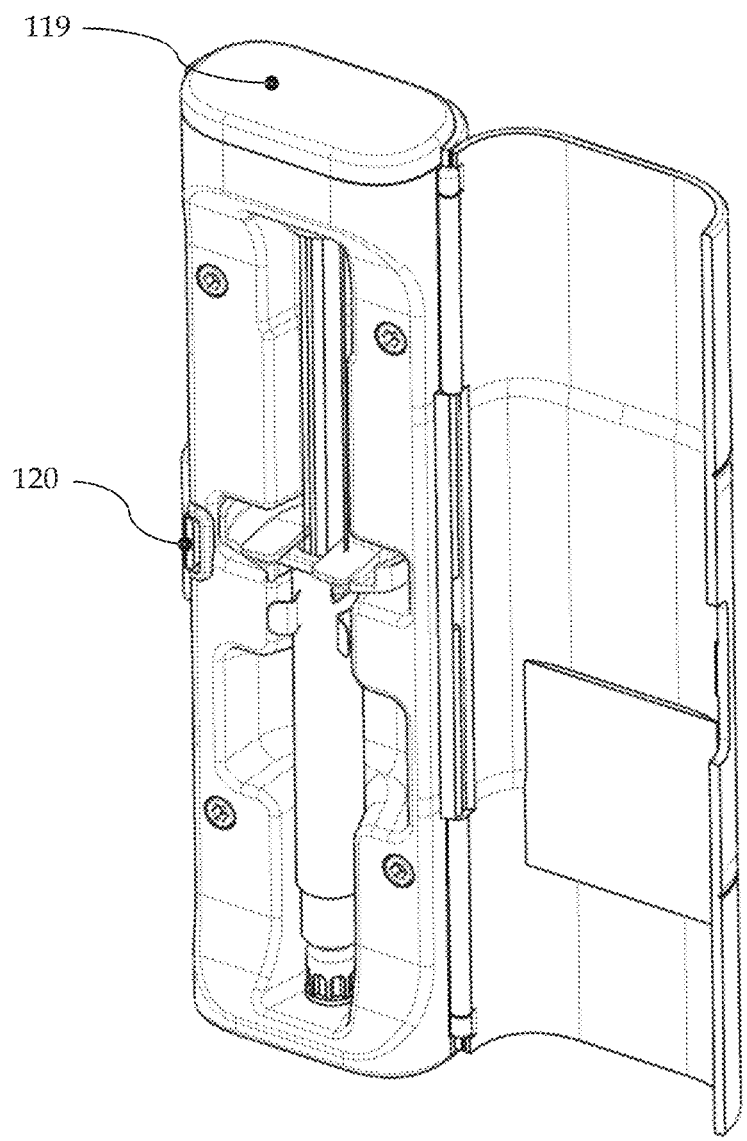
FIG. 7 illustrates a syringe case embodiment, general view showing syringe inside open case.
Figure 8:
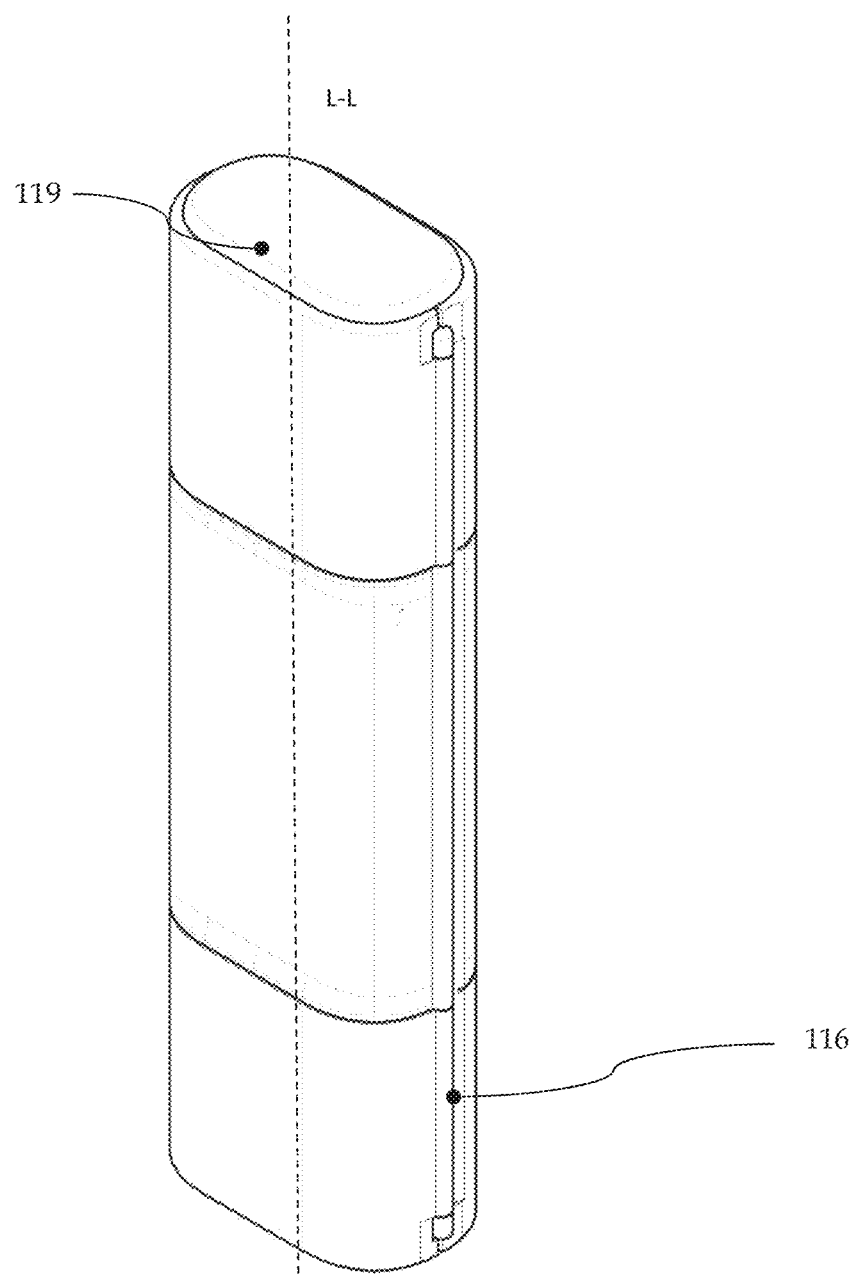
FIG. 8 illustrates a syringe case embodiment, general view showing closed case.

Additionally the housing may comprise a moveable cover or lid 113 which is moveable from a closed position, as shown in FIG. 7, completely or partially over the compartment to an open position, as shown in FIG. 8, in which the syringe 117 or vial can be inserted into the compartment. Providing a lid 113 for the housing allows the user to selectively enclose the syringe 117 or vial in the housing such that it may be enclosed during transit or during a shaking event, and then opened when drug delivery is intended.

Additionally the compartment may be dimensioned to receive the entire syringe 117 or vial snugly and hold it securely within the housing. In this case the compartment fits the form of the syringe 117 or vial to such an extent that it is held securely in the housing. This may allow the syringe 117 or vial to fit precisely in the housing such that the orientation of the syringe 117 or vial relative to the housing is known.

Figure 10:
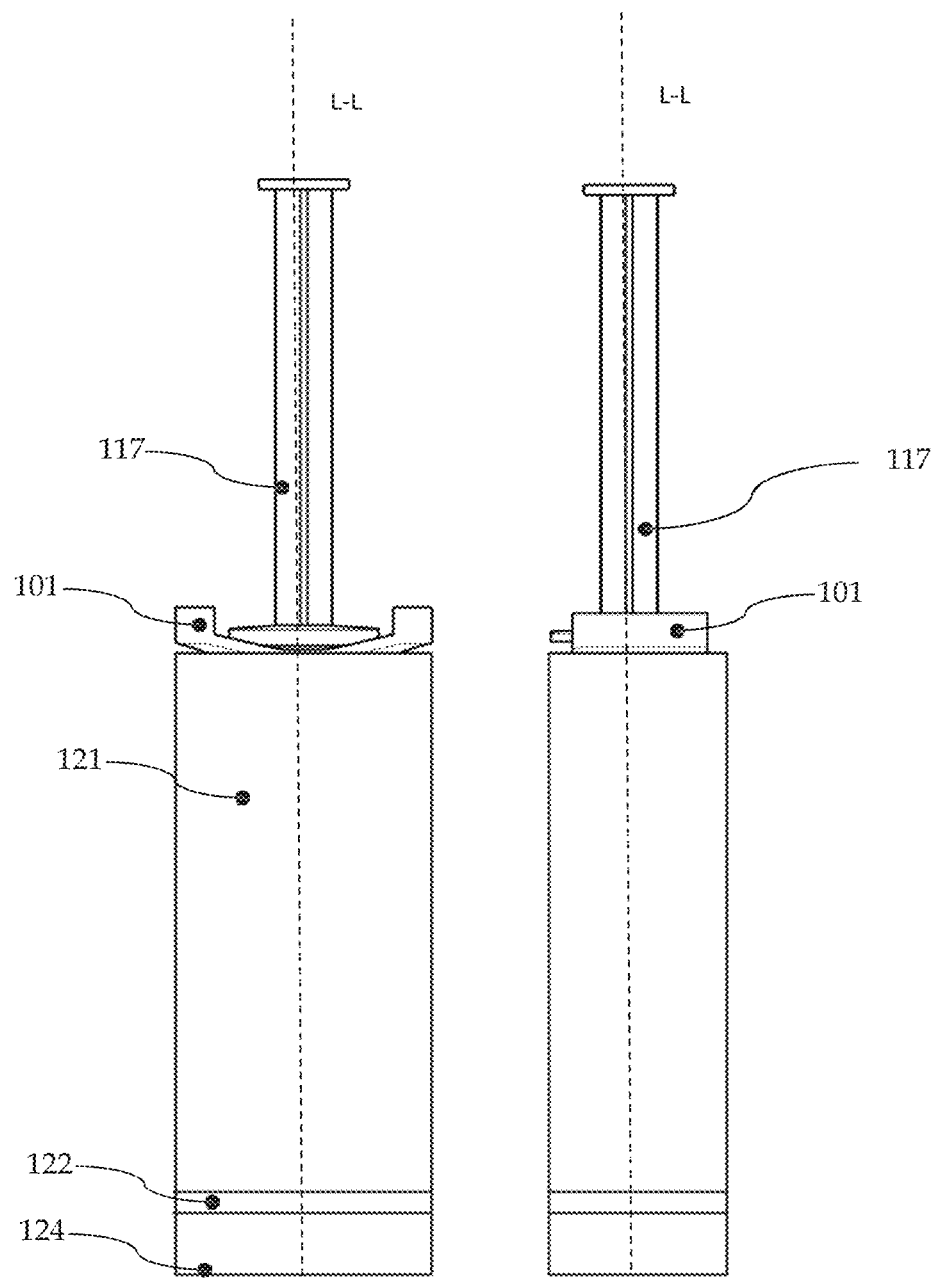
FIG. 10 illustrates a syringe pot embodiment with syringe inside, showing front and side views.

With reference to FIG. 10, the housing comprises an elongated body 121 approximately the same length as a syringe barrel such that a syringe can be inserted into a syringe receiving hole 123 in the body 121 and retained by the compressive force applied by the finger-like members between a syringe finger flange and a body base 124. In such a device, the body 121 of the housing may receive the syringe through a hole 123 in the body. The syringe may be inserted until a stop position. At the stop position, the user may retain the syringe in the housing by retaining the finger flange towards a base 124 of the body. This may be done by holding the finger flange between two fingers and the base of the body with a thumb.

The housing 202 may comprise an opening through which a discharge nozzle of a syringe or vial is extendable, or comprises an opening through which at least a portion of the syringe barrel adjacent a syringe's discharge nozzle can extend. In this aspect only a portion of the syringe or vial is contained in the housing 202. The syringe or vial may be inserted into one end of the housing 202 which may provide a form which is easier for the user to grip.

Figure 4:
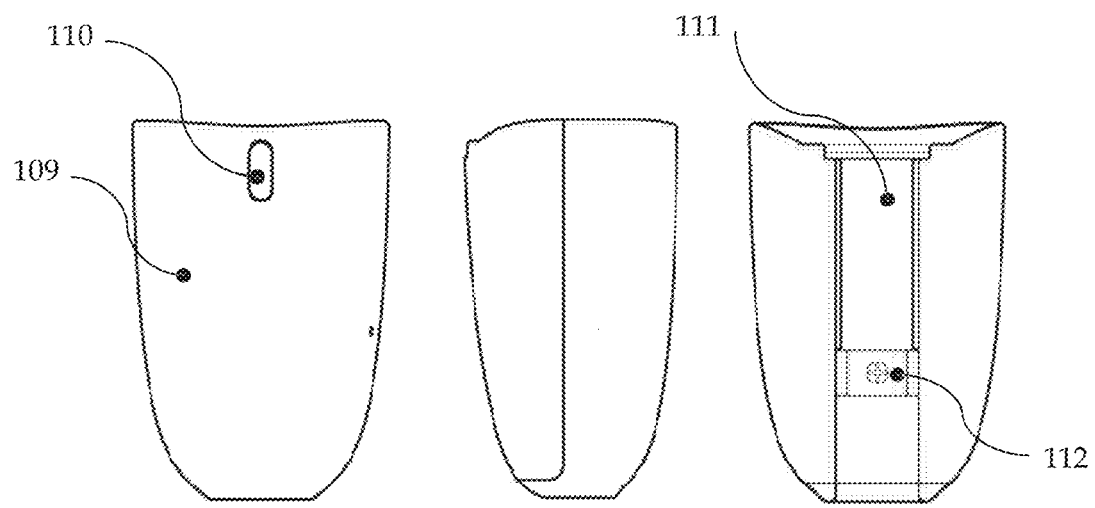
FIG. 4 illustrates a syringe barrel attachment embodiment, front, left and right side.
Figure 12:
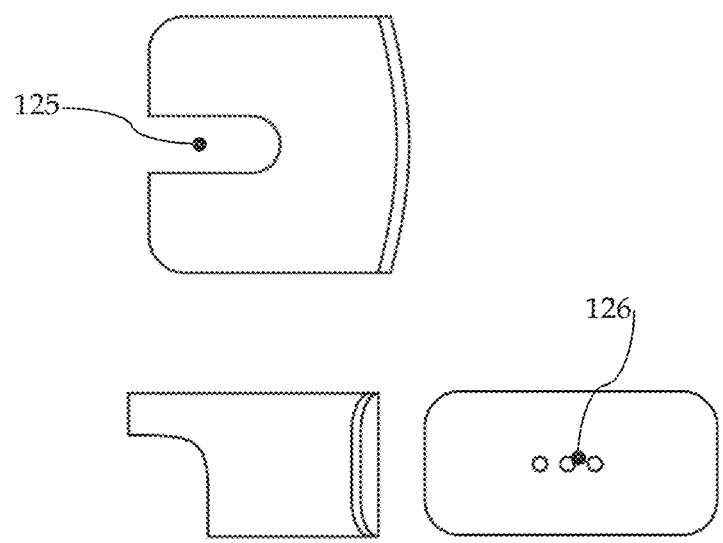
FIG. 12 illustrates a syringe finger rest attach embodiment, without syringe.

Referring to the embodiments of FIGS. 4, 6, and 12, the housing 202 comprises a body with a syringe accepting slot 125 sized to accept a syringe barrel or a vial containing the pharmaceutical components. In such a case the slot 125 may extend through the body of the device 200 such that either end of the barrel of the syringe or the vial may protrude from either end of the slot 125. The slot may allow a longitudinal axis of the syringe or vial to be aligned with the device 200 in a known relative orientation, thus allowing the orientation of the syringe barrel 107 or the vial to be known with respect to the ground or with respect to the direction of shaking during a shaking event.

Still referring to the embodiments of FIGS. 4, 6, and 12, the device may further comprise a releasable clip 112, 118 in the slot configured to retain the syringe. The clip 112, 118 may be biased such that the syringe barrel 107 may pass over it but a threshold force on the syringe is required to bias the clip 112, 118 again to remove the syringe. This may allow the device 200 to be kept with the syringe for storage. This may also aid the user in keeping the device 200 attached to the syringe 117 securely during a shaking event. The releasable clip 112, 118 may be biased by an elastic member such as a spring, or it may be biased by a moveable component such as a user operated switch or lever, allowing the user to selectively lock the syringe in the slot of the device 200.

Figure 15:
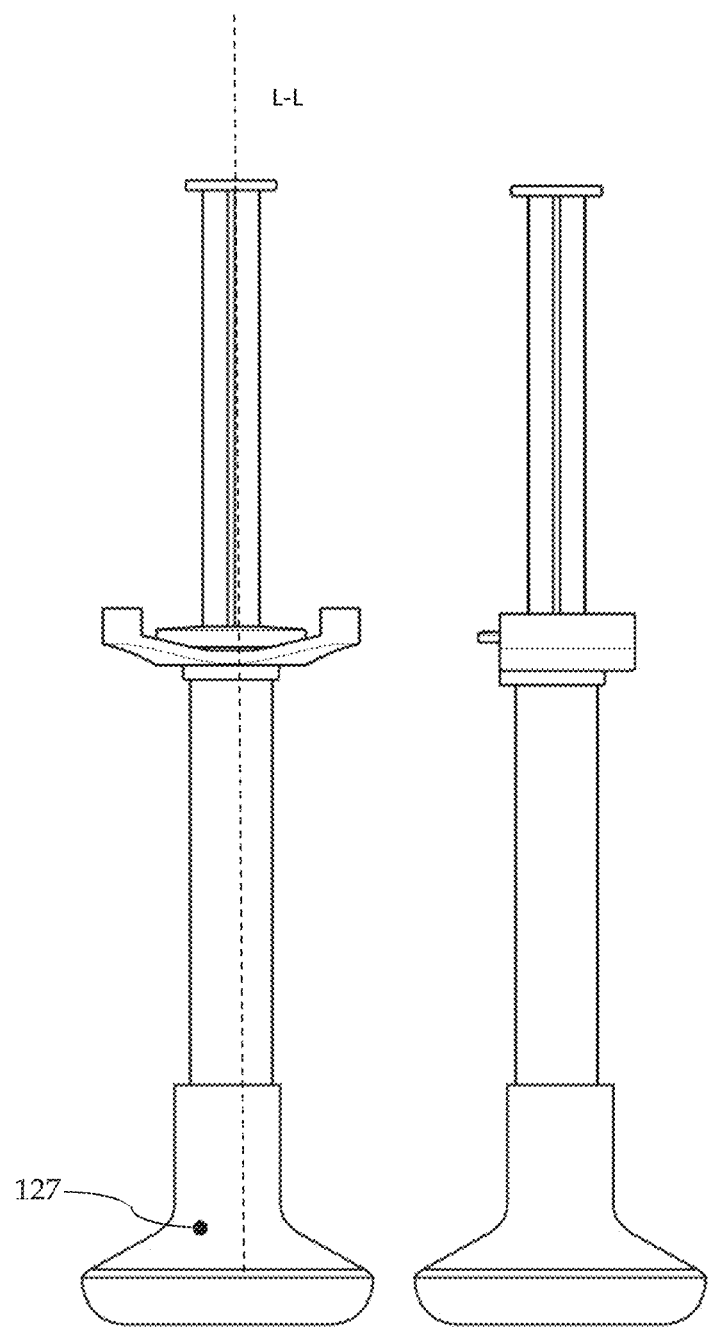
FIG. 15 illustrates a syringe puck embodiment, with syringe.
Figure 18:
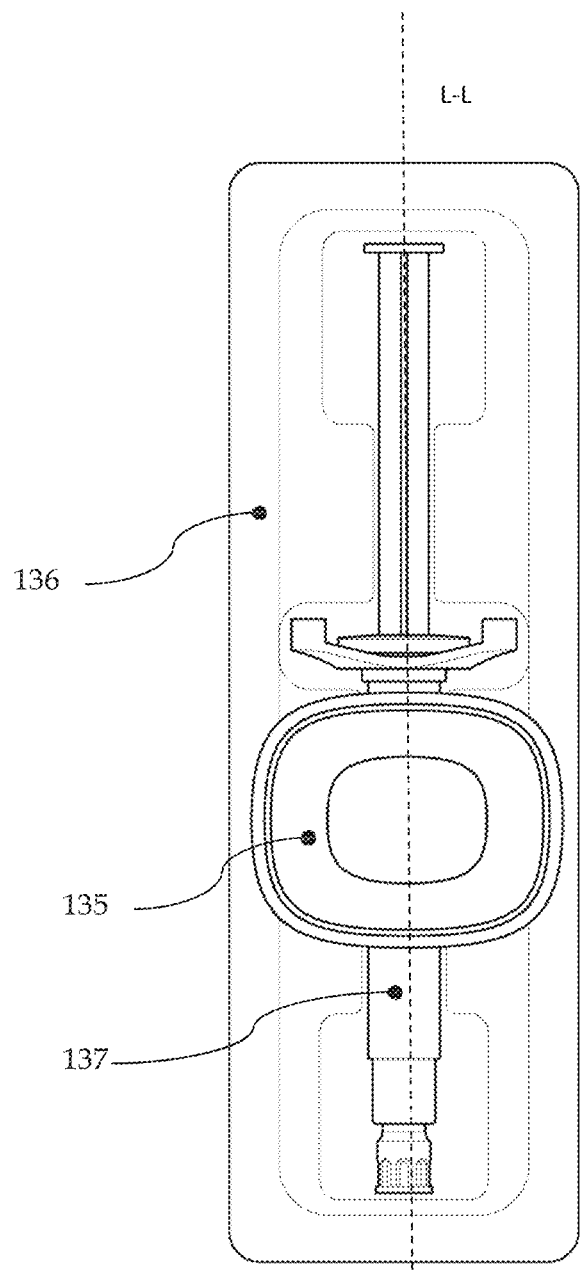
FIG. 18 illustrates a packaging attachment embodiment A, attached to syringe while in tray.
Figure 19:
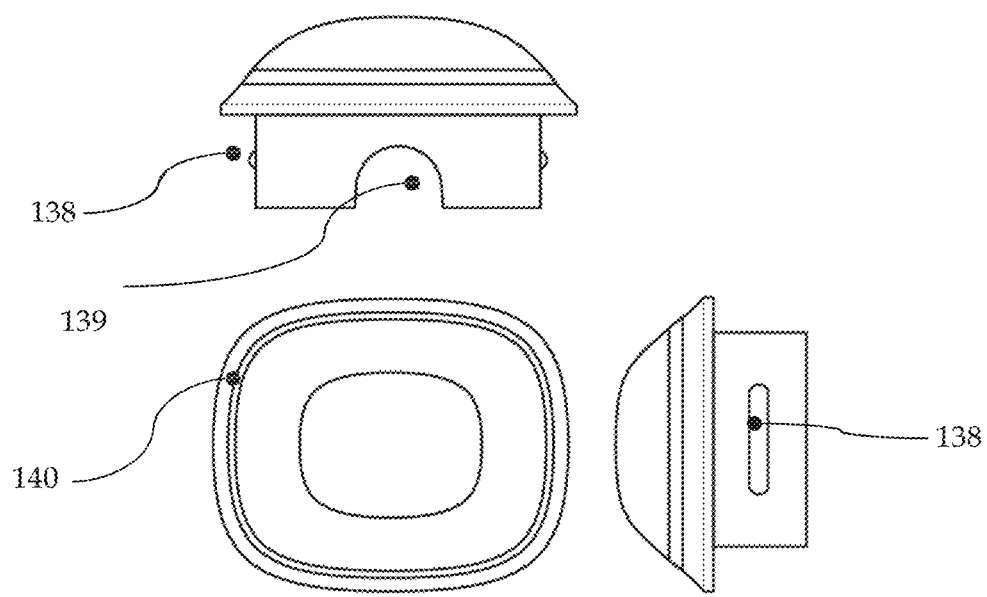
FIG. 19 illustrates a packaging attachment embodiment A, detached from syringe.

Referring now to FIG. 15 the housing 202 comprises a puck-like body 127 with a syringe accepting hole 128 so that in use a syringe is inserted into the syringe accepting hole and is held in place with a user's thumb on an underside thumb grip 130. In this aspect the user may hold the device in a grip with the thumb on the puck-like body 127. Some users may find this grip easier to maintain whilst shaking the device 200 in a shaking event.

With reference now to a syringe such as that shown in FIG. 3, the syringe may comprise a discharge member adapted upon application of force thereto to discharge the contents of the syringe. Such a discharge member may be a bung contained within the body of the syringe and provide a seal within the syringe to contain the pharmaceutical components. Applying pressure to the discharge member or the bung increases the pressure of the pharmaceutical components causing them to be discharged through an opening.

The device 200 may comprise an activator adapted to act upon the discharge member of the syringe to expel its contents through the discharge nozzle. Such an activator may be a plunger 105 which may be manually pressed by a user in order to act upon the discharge member to discharge the pharmaceutical components. Alternatively the activator may be a plunger which is acted upon by an automatic drive member such as a spring.

With reference to FIGS. 3 and 12 the housing 202 may further comprise an activator opening through which the discharge member of the syringe can extend for application of force directly by the user from outside the housing. In this aspect the housing may largely contain the syringe but the syringe does not necessarily need to be removed from the housing for the user to administer the pharmaceutical components. This may reduce the time that it takes a user to administer the pharmaceutical components following the successful completion of a mixing event.

The device 200 may be an attachment for a syringe wherein the housing 202 is adapted to fit against a barrel of the syringe. In this aspect the device may be attached to the syringe and sit against the barrel. Such a device may have a small size and may be simple to attach to a syringe.

Alternatively the device 200 may be an attachment for a syringe and the housing 202 is adapted to fit around a barrel 107 of the syringe. Similarly this device 200 may have a small size and be simple to attach to a syringe, but may at least partially surround a syringe barrel 107 to fit more snugly. The housing 202 may be adapted to fit around only a portion of the barrel 107 of the syringe, or the housing 202 may be adapted to fit around the whole of the barrel 107 of the syringe.

Alternatively the housing 202 may be formed of two hinged portions which rotate in a hinged manner with respect to each other such that the hinged portions can close around the barrel and latch thereto. The hinged portions may be connected by a rotatable hinge or by a living hinge. At least one of the two portions may include a slot to receive the barrel of the syringe. The two portions may be held together by application of a force by the user or they may be held together by a mechanical latch, such as a latching member.

Alternatively to requiring a syringe which incorporates a discharge nozzle the housing 202 may comprise a discharge nozzle which is adapted to be in fluid communication with the contents of a vial when such a vial is inserted into the housing 202. In such a device a vial may be accepted by the housing 202 such that the housing 202 provides the discharge nozzle for expelling the pharmaceutical components. Further to this the device 200 may further comprise an activator 105 adapted to act upon a discharge member to expel the contents of the vial through the discharge nozzle. In this embodiment, the vial may be replaced whilst the components of the device may be reused.

Now with reference to the devices shown in FIGS. 18 to 21, the device 200 is configured to attach to packaging 136,142 containing a syringe 144. The syringe 144 may be supplied in packaging 136, 142 which may be removed before the pharmaceutical components are administered. The mixing event may be carried out with the aid of the device 200 before the packaging is removed. Using such a device 200, the syringe 144 need not be removed from its packaging 136, 142 until the pharmaceutical components are actually to be administered.

Still with reference to FIGS. 18 to 21 the device 200 may further comprise at least one retaining member 138, 145 configured to retain the device 200 against the packaging 136, 142 containing a syringe 144. The device 200 may include an element such as a latch, a side interference clip 138, or a return clip 145 which are configured to engage with a corresponding portion of the packaging 136, 142 of the syringe 144, for example a detent or an edge of the packaging 136, 142. Alternatively or additionally the device 200 may comprise an adhesive to retain the device 200 against the packaging 136, 142. Further, the device 200 may be held against the packaging 136, 142 by application of a force by the user.

The pharmaceutical components for mixing comprise at least two phases. The at least two phases may separate after a time of inactivity. The components may include more than two phases. As an example, in a case where there are two phases, both phases may be liquid phases or one phase may be a liquid phase whilst the other is a solid phase. In either case the components may be mixed by shaking the container in which they are enclosed. In the case where there are three phases, there may be a combination of two liquid phases and one solid phase, one liquid phase and two solid phases, or three liquid phases. A liquid phase may comprise a component for suspension of a solid phase wherein the solid phase comprises a pharmaceutically active component. Alternatively or additionally any liquid phase may also comprise a pharmaceutically active component.

Further disclosure of various features is now described with reference to the figures. Notably, FIG. 1A illustrates a schematic overview of the electronic system that can be utilized with various embodiments described and illustrated herein. It is noted that for these embodiments, the forces are measured preferably using a 3-axis accelerometer 150 because the user's shaking movement will likely be in more than one direction and furthermore sufficient acceleration may be a factor of accelerations in multiple directions. Hence, a threshold may be determined to be a function of one or more acceleration directions.

Additionally the system may include a start switch 153, which may be a manually activated switch, or preferably may be an acceleration activated switch to wake up the circuit, thus conserving battery power when the device is not in use. The advantage of the acceleration activated switch is that the user need only start shaking the device to switch it on. In some embodiments it may be preferable to require the user to make a conscious decision to switch the device on, and carry out a specific explicit action to switch the device on, hence the manual switch may be preferable. Once the device has woken up, the battery latch 152 ensures power is supplied from the battery 151 for sufficient time to complete the shake cycle and provide feedback to the user.

A further development of this embodiment is described as follows. Time is measured using a microcontroller 154, microprocessor or timer; from the moment that shaking is first detected. The electronic system is programmed with an algorithm which compares the measured shake acceleration and duration with a preset threshold. The electronic system compares the recorded elapsed time and force measurements and returns a communication signal corresponding to the device state 155. The device state is communicated using one or preferably a combination of the following: visual feedback such as light emitting diode (LED), graphical display such as Liquid Crystal Display (LCD); audible feedback such as an audible buzzer or polyphonic speaker; tactile feedback such as vibration motor. Such an electronic circuit requires a power source, such as a battery, that may be rechargeable or not. If not rechargeable, the battery may be replaceable or it may not be replaceable, in which case the device must be disposed of in its entirety at end of life, defined by the end of the battery life. If the battery is rechargeable, it may be replaceable or it may not be replaceable, in which case the device must be disposed of in its entirety at end of life, defined by the end of life of the battery when it no longer holds enough charge to usefully power the device. This may be defined by a number of charge cycles.

The electronic circuit is contained inside the device, with visual feedback means visible to the user by way of a window or light transmitting element. The electronic circuit affords additional design features:

Pause function. The program may allow the system to detect when shaking has ended prematurely, or if the level of shaking vigor has reduced to a level below the pre-set threshold, using the accelerometer or acceleration activated switch. If such events are detected the device may enter a pause mode, which pauses the timing process and may indicate to the user that the device has entered pause mode. The indication to the user may be a pause in the feedback being provided, such as a pause in the audible tone, or a pause in the tactile vibration; or it may be by other means such as a state change on a light or screen. The user, upon receiving the pause indication may then correct their actions, by recommencing the shake action or increasing the vigor of the shake action, at which moment the device switches out of pause mode and recommences with the timing and force monitoring process, starting from the time count at which it paused. If the device is in pause mode for a significant amount of time such that the particles may have started to re-form a sediment, the timer will be reset. Reset of the timer may or may not be indicated to the user via a user notification device. This could for example be notified to the user by a message on a display, the emission of an audible tone, a tactile vibration or as a state change on a light or screen.

Syringe administration timer. A timer may be used to warn the user that too much time has elapsed since the device was shaken. After shaking, the particles will slowly return to a sediment state; therefore there is a maximum time limit between shaking the device and administering the injection. In some scenarios, the user may shake the device correctly, but then may be distracted long enough for the particles in the syringe to re-sediment. A timer may be set such that when the max allowable time after shaking of the housing has elapsed, the user is warned to shake the device again before administration. This warning could be communicated using several methods. As examples, an audible buzzer could sound when the maximum time has elapsed, or a green light which was illuminated to indicate shaking has completed could switch off.

Low battery warning. Such an electronic system requires a power source, preferably a battery cell. When the remaining power in the battery has reduced to a point where device functionality may soon become impaired, the device may indicate to the user that a battery failure is imminent, and that the battery must be replaced. The device could shut down in such an event so that it may not be used until the battery has been replaced. This would prevent a potential device malfunction. The state of the battery may be measured as the remaining charge or power in the battery, the voltage supplied to the circuit, the current supplied to the circuit, or the stability of the battery under varying loads. Alternatively in the case of a rechargeable battery the health of the battery may be monitored to indicate when device functionality may be impaired. If the device notifies the user that failure of the power source is imminent then the user may take action to replace the battery or the whole device. In the case where the battery is not replaceable, the finite lifetime of the battery may be less than the lifetime of the other components, and may beneficially indicate to the user that the device should be replaced before any other components reach their lifetime.

Error warning. Such an electronic system can perform self-checks on the system and main components so that when errors are detected the user may be given warning. It can perform such self-checks whenever the device is awoken for a shake cycle and immediately communicate that it has entered an error mode. This prevents the user from using a faulty device and prompts them to take remedial action, for example to return the device to the manufacturer, and use a replacement device.

Information distinguishing force and time. In the first instance this invention is described as providing the user with information on the success of the shake action as a single piece of information, when both sufficient time AND sufficient vigor have been achieved. An alternative arrangement of such an electronics system can provide feedback to the user on the constituent elements; in that two pieces of information are provided, the elapsed time and the level of vigor over that time. That way if a user fails to achieve the combination of sufficient time and vigor they may consult the information provided and determine the reason they were unable to be successful, they may determine if they failed to shake for sufficient time, or if they failed to shake with sufficient vigor.

Drug expiration alert. A development of such an electronic system incorporates means to read the expiration data on the syringe and warn the user if it has expired. If the user were informed that the expiration date had expired they could dispose of the expired syringe and use another that had not expired. Such a system uses scanning components that read a barcode or text on the syringe to gather the expiration date, or may communicate with a chip on the syringe that contains the lot and expiration information, and compares the date to an internal clock and calendar programmed into the processor and gives an alert if the gathered date is before that on the internal clock and calendar.

The features described and illustrated above can be embodied in the following Embodiments 1-8 with highlights in the variations and differences between each embodiment described with reference to the drawing figures indicated below.

Embodiment 1. MIMIC. The trainer embodiment (FIG. 1B and FIG. 2) uses a form factor for a housing that mimics that of a syringe. It may include a syringe barrel element 103, with finger flange 100 at one end and a barrel tip 104 at the other. The distance between finger flange 100 and barrel tip 104 are similar to that of a syringe such that it may be held in a similar fashion. At the top of the form is a cylindrical portion 100 that represents a syringe plunger rod. The barrel 103 includes a light emitting feedback window 102, through which light is emitted to communicate the state of the device. In the preferred embodiment, amber light is used to indicate the device is running through a shake cycle and is monitoring the level of agitation imparted on it; green light is used to indicate the shake cycle is complete and sufficient shaking has occurred. When not in use, the light is off to conserve battery power and also to indicate that the shake cycle has not yet commenced.

Figure 5:
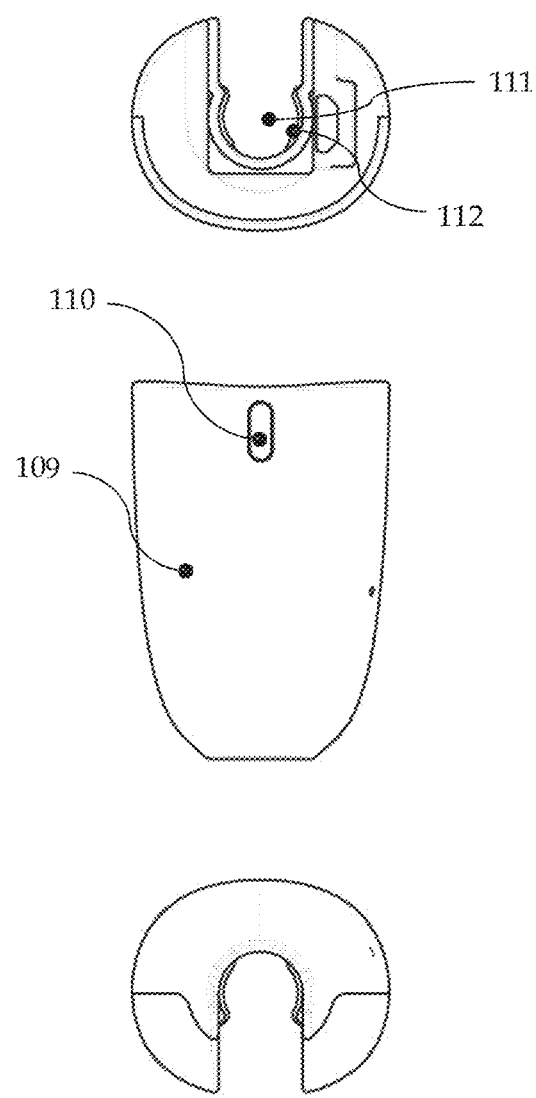
FIG. 5 illustrates a syringe barrel attachment embodiment, front, top and bottom side.

Embodiment 2—ATTACH. The embodiment shown in FIG. 3-FIG. 5 attaches to the syringe and provides feedback to the user while they are shaking the syringe. The device housing may include a body 109 with a slot 111 sized to accept a syringe barrel 107. A clip 112 (FIG. 4) in the slot 111 retains the syringe. Once the device housing is attached to a syringe, the shaking motion is measured using the internal electronic system, and the device state is communicated in two simultaneous ways. The first communication method is with light emitted from the light emitting feedback window 110. An amber light indicates that a shake cycle is in progress, and a green light indicates that it is completed. The second simultaneous feedback method is audible. An intermittent audible buzzing tone indicates that the shake cycle is in progress, which changes to a continuous tone when the shake cycle is completed. Furthermore, the intermittent tone emitted during the shake cycle is set at a frequency of approximately 3 Hz to reinforce the frequency and speed of shake required for optimum mixing, exploiting the tendency for humans to match repetitive behavior to percussive audible tones.

Figure 9:
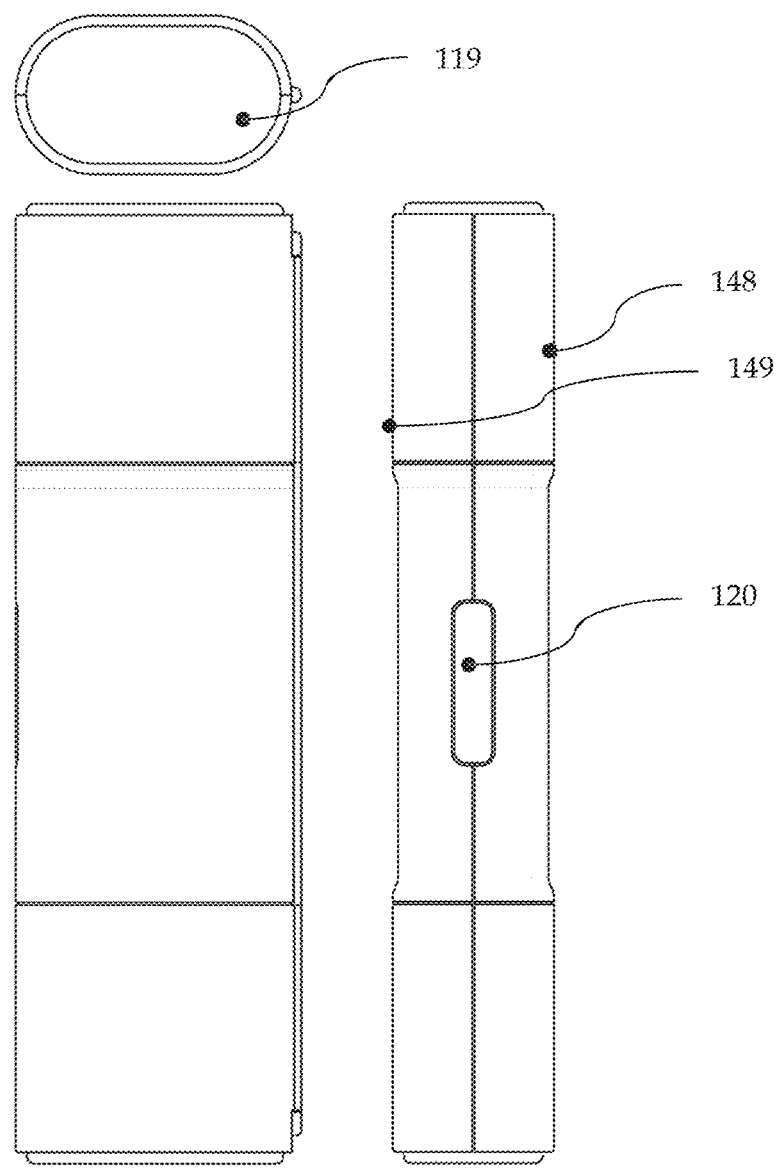
FIG. 9 illustrates a syringe case embodiment, general view showing front, top and side view.

Embodiment 3—CASE. The embodiment shown in FIG. 6-FIG. 9 contains the syringe and provides feedback to the user while they are shaking the syringe. The device housing is opened by pressing on the lid catch 120; a syringe 117 is placed in the case liner 115 where it is retained by a spring clip 118 as shown in FIG. 7. Alternatively, the syringe could be retained by case lid 113 when the device housing is closed. Case lid 113 pivots around the case syringe 116 enclosing the syringe as shown in FIG. 8. The case includes flat surfaces on the case base 148 and case top 149 (FIG. 9), such that when placed on a desktop or work top it will not roll off. The case is closed and retained in a closed position by the lid catch 120. The outer shape of the case is designed to allow for users to hold it comfortably and securely when shaking. Shaking motion is measured using the internal electronic system, and the device state is communicated in two simultaneous ways. The first communication method is with light emitted from the light emitting panel 119, and amber light indicates that a shake cycle is in progress; and a green light indicates that it is completed. The second simultaneous feedback method is tactile. An intermittent vibration transmitted to the holding hand indicates that the shake cycle is in progress which changes to a continuous vibration when the shake cycle is completed. Furthermore the intermittent vibration emitted during the shake cycle is set at a frequency of approximately 3 Hz to reinforce the frequency and speed of shake required for optimum mixing, exploiting the tendency for humans to match repetitive behavior to percussive stimuli. The light emitting panel turning green indicates to the user to remove the syringe and continue with the drug administration process. This embodiment may be further developed with a syringe lock out feature. This feature would detect the presence of the syringe inside, lock the case in the closed state and only unlock the case when sufficient time and shake vigor have been achieved. In addition, if the user does not open the case to remove the syringe for injection within a specified time period, the case could re-lock itself, and/or the light could turn amber again, indicating that the device housing must be shaken again to re-suspend the particles before the syringe can be used.

Figure 11:
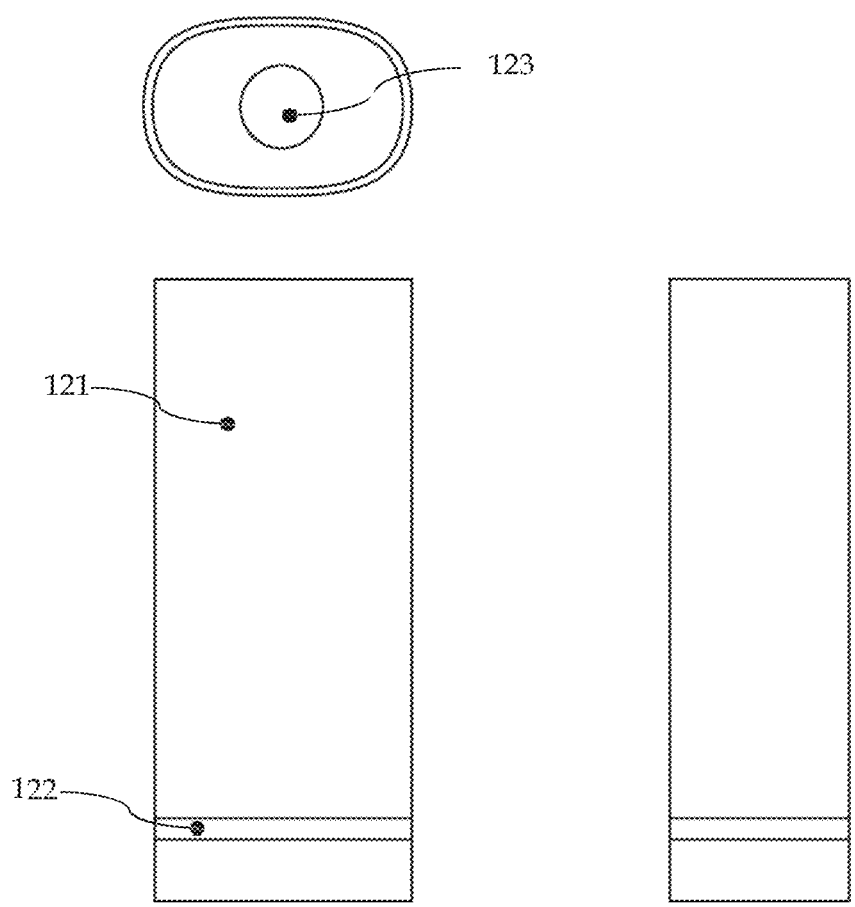
FIG. 11 illustrates a syringe pot embodiment without syringe showing front and side views.

Embodiment 4—POT. The embodiment shown in FIG. 10 and FIG. 11 includes an elongated body housing approximately the same length as the syringe barrel. The syringe is inserted into a syringe receiving hole 123 in the body housing and is retained by the compressive force applied by the fingers between the syringe finger flange 101 and the device body housing base 124. When the coupled device and syringe are shaken, motion is measured using the internal electronic system, and the device state is communicated in two simultaneous ways. The first communication method is with light emitted from the light emitting band 122, and amber light indicates that a shake cycle is in progress; and a green light indicates that it is completed. The second simultaneous feedback method is tactile. An intermittent vibration transmitted to the holding hand indicates that the shake cycle is in progress which changes to a continuous tone when the shake cycle is completed. Furthermore, the intermittent vibration emitted during the shake cycle is set at a frequency of approximately 3 Hz to reinforce the frequency and speed of shake required for optimum mixing, exploiting the tendency for humans to match repetitive behavior to percussive stimuli. The light emitting panel turning green indicates to the user to remove the syringe and continue with the drug administration process. As with other embodiments, further means of supplemental communication may be included, such as audible or tactile vibrating feedback, and a timing function can be used to signal the user if the syringe has not been removed from the device before a specified time period, indicating that the device must be shaken again to re-suspend the particles prior to performing the injection. A switch internal to receiving hold 123 would be used to detect when the syringe is attached to the device.

Figure 13:
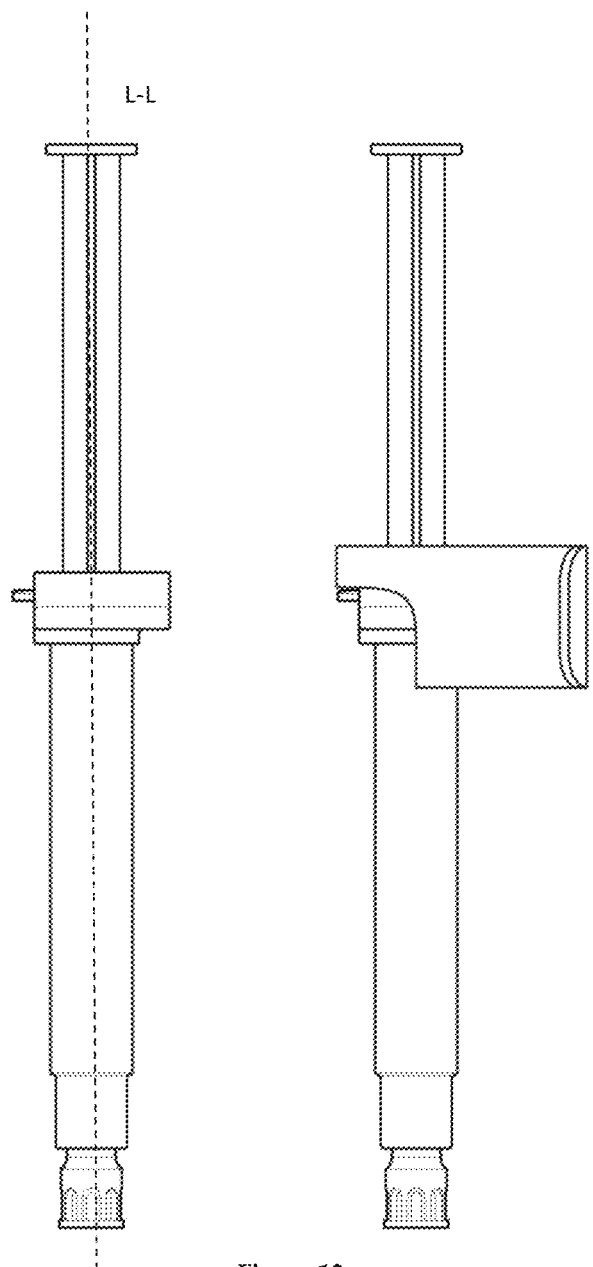
FIG. 13 illustrates a syringe with and without syringe finger rest attach embodiment, with—side view.
Figure 14:
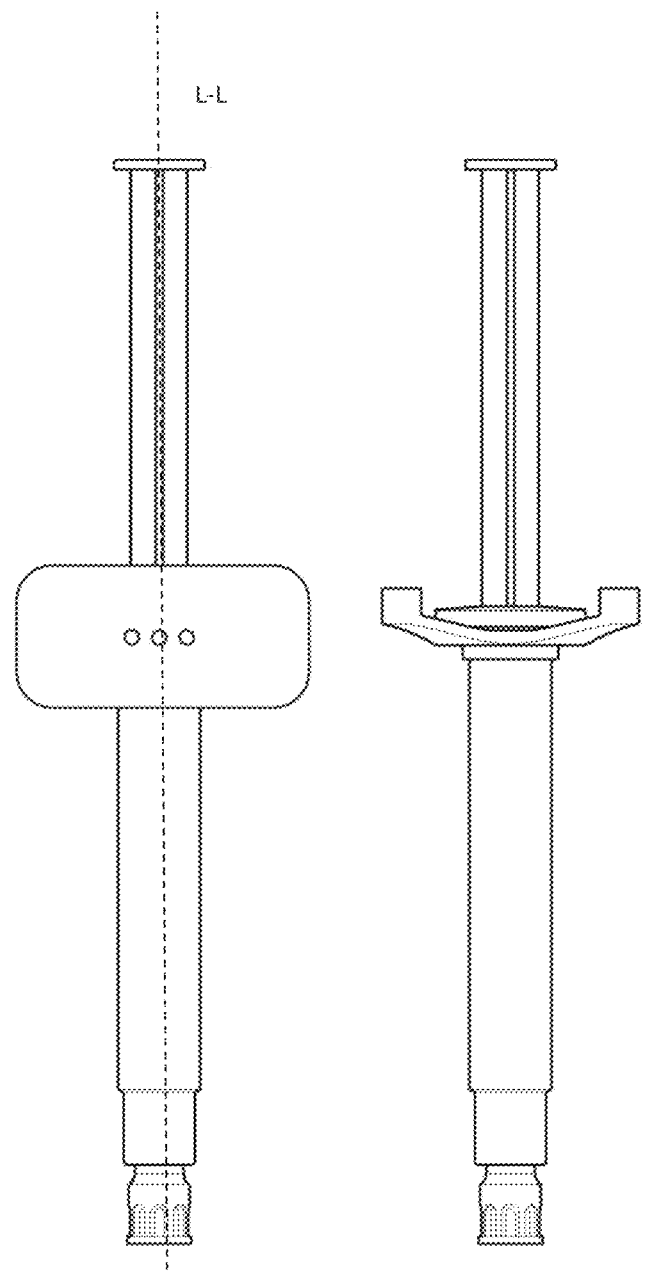
FIG. 14 illustrates a syringe with and without syringe finger rest attach embodiment, with—front view.

Embodiment 5—FINGER REST ATTACHMENT. The embodiment shown in FIG. 12, FIG. 13 and FIG. 14 is similar to embodiment 2, in that it attaches to the syringe. It is shown on the syringe in FIG. 13 and FIG. 14. The syringe fits and is retained in the syringe accepting slot 125. The electronic system is housed within, and communicates to the user via the light panel 126 on the front face. An orange color indicates when the device is sensing and this turns green when it has been shaken sufficiently. As with other embodiments, further means of supplemental communication may be included, such as audible or tactile vibrating feedback.

Embodiment 6—PUCK. The embodiment shown in FIG. 15 and FIG. 16 is similar to embodiment 4, in that it fits to the bottom of the syringe but is a much more compact design. It may include a body housing 127 with syringe accepting hole 128. The interface is provided by a circumferential light emitting band 129 around the diameter of the base of the form. In use, the syringe is inserted into the syringe accepting hole 128 and is held in place with the user's thumb on the underside thumb grip 130. As with other embodiments, further means of supplemental communication may be included, such as audible or tactile vibrating feedback.

Embodiment 7—EVOKE. The embodiment shown in FIG. 17 is similar to embodiment 1 of FIGS. 1B and 2. It is a stand-alone device, which does not interact with the syringe, intended to be used in advance of the administration process. The user may practice shaking in advance of shaking the real syringe. It may include the device body housing 134, at either end of is the finger grip 131 and the thumb grip 132. The distance between finger grip and thumb grip is similar to the distance between the syringe finger grip and rubber stopper, to ensure it feels similar in the hand. When the user shakes the device, the device detects the forces applied and emits an amber light from the light emitting window 133. The light turns green when sufficiently vigorous shaking has occurred for sufficient time. As with other embodiments, further means of supplemental communication may be included, such as audible or tactile vibrating feedback.

Figure 20:
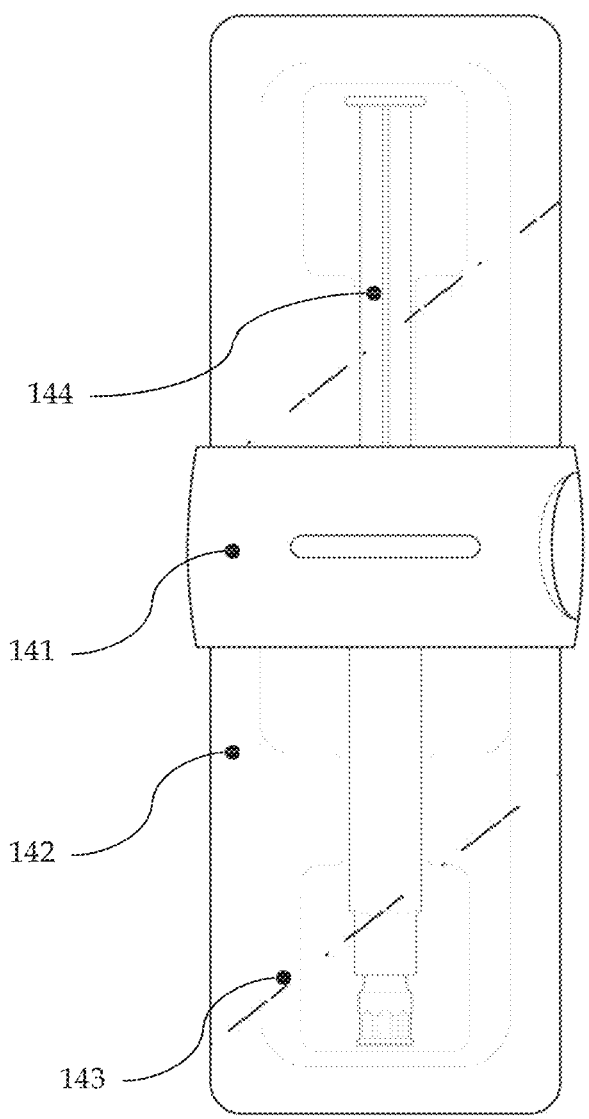
FIG. 20 illustrates a packaging attachment embodiment B, attached to syringe tray.
Figure 21:
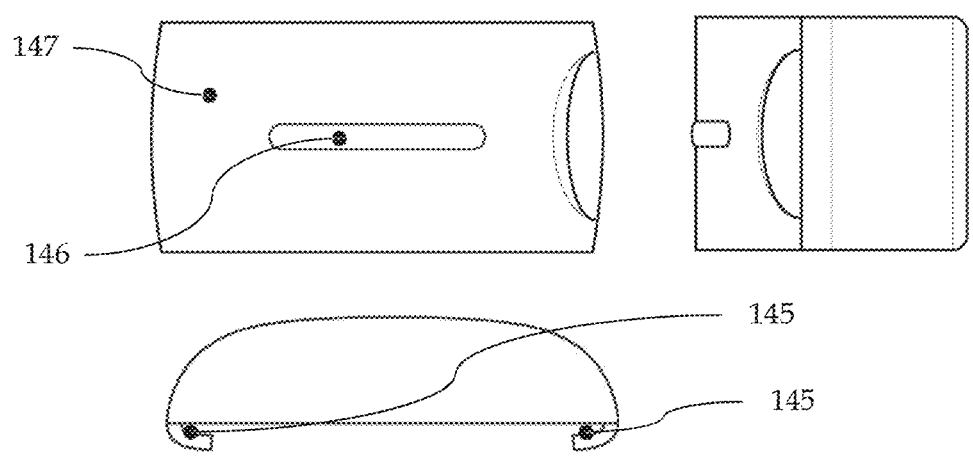
FIG. 21 illustrates a packaging attachment embodiment B, detached from syringe tray.

Embodiment 8—PACKAGING B. With reference to FIG. 20 and FIG. 21, this embodiment is similar to embodiment 8, in that the device 141 attaches to the syringe blister packaging 142 while the syringe 144 is contained within. In this embodiment, the protective film 143 is still in place on top of the blister tray 142. With reference to FIG. 21 the device is attached to the blister tray by sliding it along the length of the blister tray and is retained against the blister tray by means of return clips 145 on the underside of the device. The body housing of the device 147 includes means of communication, a light emitting strip 146. As with other embodiments the electronic system in the device detects the onset of shaking and starts to monitor the vigor and duration of shaking. While doing so, the light emitting strip 146 emits amber light. Once sufficient vigor and duration have been achieved the light changes to green. After shaking is completed the device is removed from the blister tray 142; the blister tray film 143 is peeled off and the device is used normally as per the syringe administration instructions. As with other embodiments, further means of supplemental communication may be included, such as audible or tactile vibrating feedback.

It is noted that during formulation development for Invega Sustenna Three Month, the required duration and vigor required were identified and quantified as 15 seconds of vigorous shaking. Vigorous shaking was initially defined using a training video in which an expert experienced in the correct preparation of the pharmaceutical product shakes a syringe for the required 15 seconds at the required level of vigor. Video analysis was used to estimate the amplitude and frequency of the demonstrated shake, finding that shake amplitude of approximately 40 cm was used at a frequency of 3.4 hertz. Assuming simple harmonic motion it was calculated that the syringe was experiencing a maximum acceleration of 9.3 g. This provides an indication of the required accelerations imparted on the fluid to achieve sufficient mixing as recommended by an expert in the preparation of such a formulation.

Figure 22:
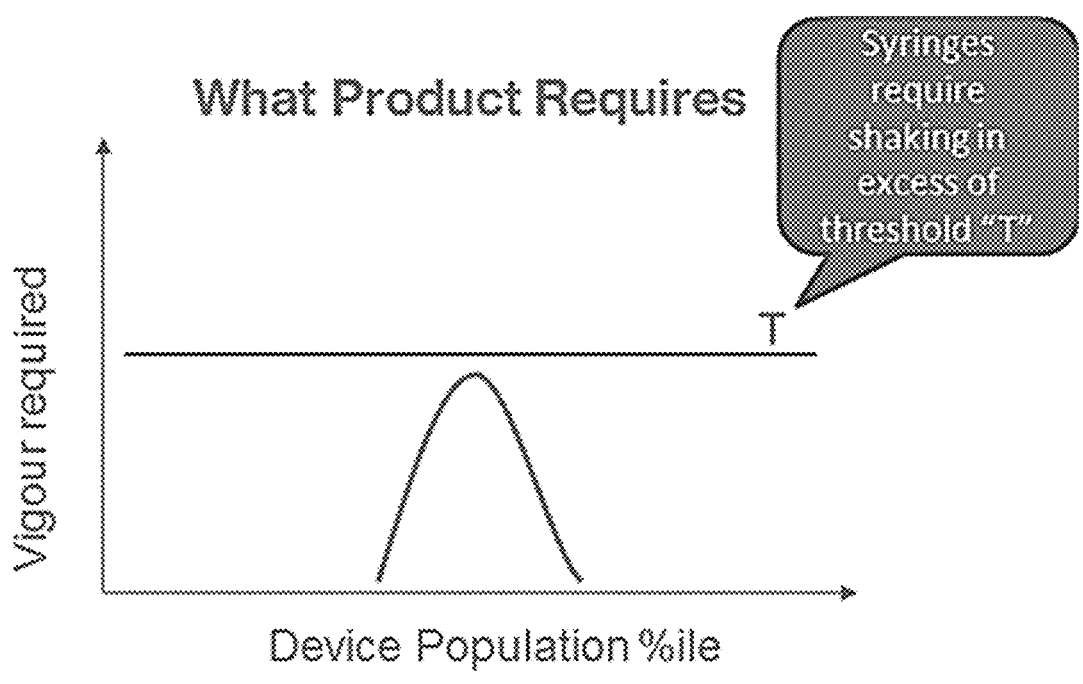
FIG. 22 is a chart illustrating the threshold requirement for a device containing sediment.

The failure mode associated with not mixing the syringe sufficiently is a failure to administer the full dose from the syringe. This occurs because insufficiently shaken syringes contain residual sediment which can block, or partially block, the syringe or needle during administration. Therefore syringes containing fluids with different sediment properties such as mass, density, and concentration can be quantified in terms of the required mixing vigor by applying controlled and known levels of acceleration (by experimental means) measuring the force required to eject the fluid from a syringe. Using such methods, different shake vigor thresholds may be determined for different fluid with different properties. FIG. 22 illustrates the device requirement for a threshold exceeding the intrinsic variability in the device population.

Figure 23:
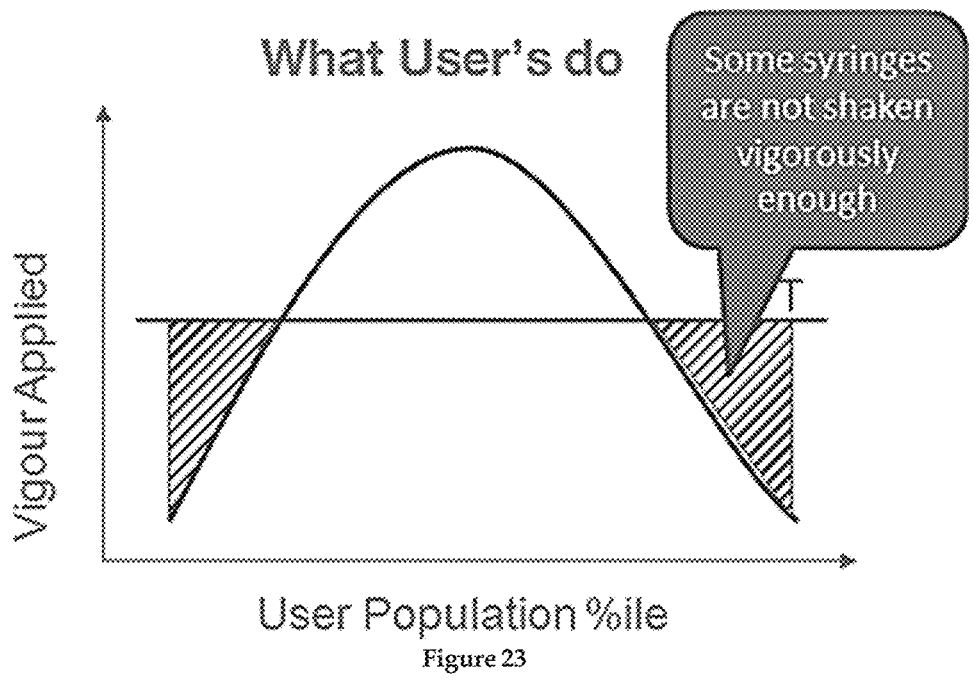
FIG. 23 is a chart illustrating how a proportion of users will fail to provide sufficient vigor to adequately mix the product un-aided.

Once the required threshold is determined, the behavior of users should also be understood. Different users will have different capabilities, strengths, habits and expectations; therefore, there is in inherent variability in the way each interprets the instruction "shake vigorously" and some will naturally fail to meet the required threshold as illustrated in the chart in FIG. 23. Moreover, different users employ different shaking techniques, which some of which will be more vigorous than others.

Figure 24:
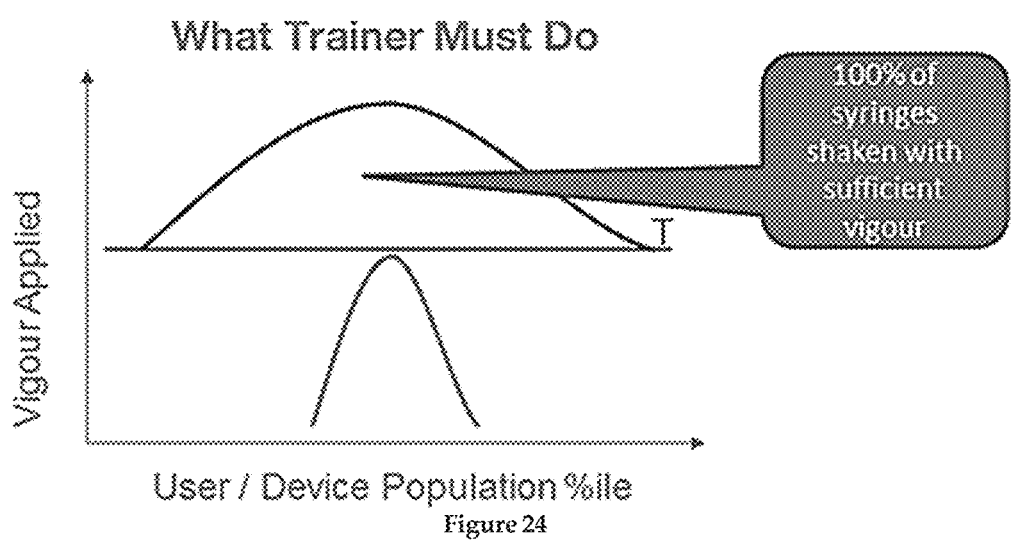
FIG. 24 is a chart illustrating the role of a device or aid, to modify user behavior so all shake with sufficient vigor to exceed the require threshold.

Acknowledging this variability, and that a minimum shake time and vigor are required leads to the conclusion that a need exists for the device described in this disclosure. The device can communicate the required time and vigor to the user, and modify behavior, increasing the likelihood of the user achieving the minimum required level of mixing. The subsequent effect of the device on the behavior across a population of users is illustrated in FIG. 24.

Once the threshold requirements and behavior modification goals are understood, consideration can be given to the various embodiments of form and function that might elicit the desired behavior modification. Such embodiments may either be used as a stand-alone device or as an in process device.

A stand-alone device is used in isolation of the administration process, providing the user an opportunity to shake a device and learn what level of vigor is required when they come to shake the real device. Such a stand-alone device may have a form factor close to that of the syringe so it may represent the experience of shaking the real syringe a closely as possible. Other form factors may also be used. For example, if the drug comes in a vial, a vial shaped device would be more appropriate.

Figure 25:
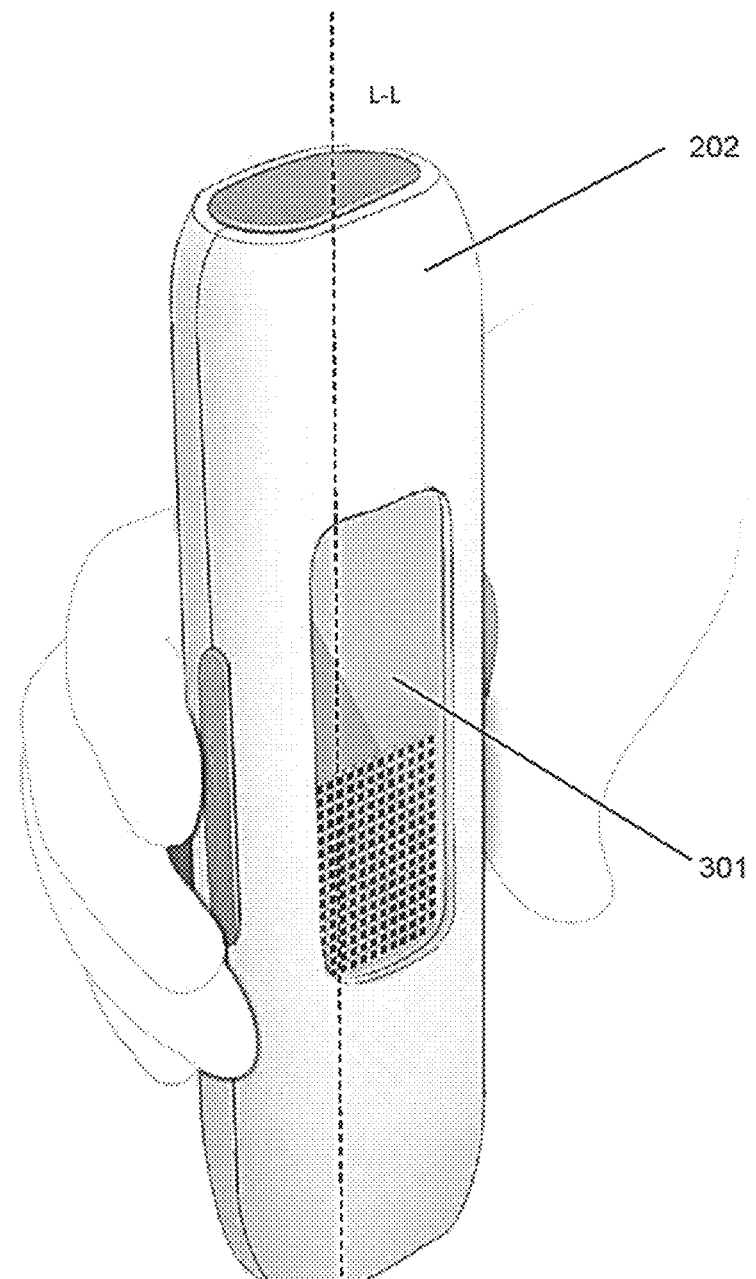
FIG. 25 illustrates a syringe case embodiment with LCD display—sedimentation mixing represented using display.

An assistive device is required to couple with, attach to, or encase the real syringe. As such means of coupling, attaching or encasing are required. This leads to varied opportunities for several form factors illustrated in FIGS. 1-21. Several means of communicating the device state to the user are possible. As previously described, they may include lights of different color or state (flashing or steady state); they may include audible means such as buzzers and speakers; and they may include tactile means such as vibrations. Further means are possible as shown in FIG. 25, such as a LCD 301 (liquid Crystal Display) or similar, which may use graphical means to communicate the device state. An LCD may be used as a segment display to communicate device state through words and icons, or it may be used as a metaphorical indication of the mix state of the solution such as described in FIG. 26. In this case, LCD segments or pixels are switched on or off to create a visual indication of particles mixing with solution. On the left side 302 of FIG. 26, darkly colored pixels in the lower portion of the display represent the presence of sediment in the bottom of the syringe. When shaking is detected by the electronic system, different pixels are switched on and off across the whole screen to indicate mixing is in progress, and when sufficient mixing is achieved the LCD can show a uniform homogenous color across the whole screen, indicating that the solution is also in a uniform homogeneous state. In order, as the device is shaken and the mixing progresses from the first state 302 indicating that sediment will be present, switching different pixels on and off across the screen the state progresses through the second state 303. As shaking and mixing continues, fewer pixels are turned on and the screen appears more sparse of pixels in the third state 304, until the whole screen is homogeneous in a final state 305.

By virtue of various embodiments of the invention, certain benefits were realized where the invention is configured as a stand-alone training device: (a) It makes the user aware of what the required shake time is; they learn through experience, (b) It allows the user to experience what the required level of shake vigor is, (c) It teaches the user what duration and level of vigor is required for the real device without impeding the normal administration process flow (d), It allows a device to have a form factor very close to that of the real syringe, (e), It allows the user to develop their skills so they are able to shake syringe sufficiently without having to rely on assistive aids, and (0 It is independent of the actual injection process and thus does not overly complicate it.

Other benefits were also realized when the invention is configured as an actual or "in-process" device: (a) It makes the user aware of what the required shake time is; they learn through experience, (b) It allows the user to experience what the required level of shake vigor is, (c) When attached to the syringe it allows the actual syringe to be shaken, providing the user with real time reassurance that it has been shaken adequately, and (d) If used correctly it reduces the chance of a real syringe being shaken insufficiently.

It is noted that these embodiments have been prototyped for testing with multiphase injectable pharmaceutical solutions. From such testing, a version has been selected for commercialization with a product with the trademark of INVEGA TRINZA™, which product is planned for distribution by Janssen Pharmaceuticals, Inc. Titusville, N.J. 08560. It is also noted that the proposed commercial version of the invention is intended to be utilized with INVEGA TRINZA™ which is described in further detail below.

In one particular embodiment, a device for training users in a proper mixing of pharmaceutical components is provided including a housing that extends along a longitudinal axis and containing an electronic system as shown in FIG. 1A. A battery is disposed in the housing for providing power to the device. The device includes a 3-axis accelerometer for measuring the spatial acceleration or forces applied to the device. The 3-axis accelerometer allows the measurement of a user's shaking movement in more than one direction. Additionally, an acceleration activated start switch is provided to wake up the device when a user has started to shake the device. A battery latch is connected to the battery so as to ensure that once the device has woken up, power is supplied from the battery for sufficient time to complete a shake cycle and provide feedback to the user. A microcontroller is provided in the device, and connected to the acceleration activated switch, the 3-axis accelerometer and the battery latch. Time is measured using the microcontroller, from the moment that shaking is first detected. The electronic system is programmed with an algorithm which compares the measured shake acceleration and duration with a preset threshold. The electronic system compares the recorded elapsed time and force measurements and returns a communication signal corresponding to the device state. Further, the device is provided with at least one light emitting diode (LED) for visual feedback and a vibration motor for tactile feedback. The electronic system is contained inside the device, and the visual feedback is made visible to the user by way of a window or light transmitting element.

In use, the user activates the device by beginning to shake the device. The microcontroller measures the elapsed time. Whilst the user is shaking the device, accelerations are measured using the 3-axis accelerometer. The microcontroller determines by the algorithm, whether the level of shaking vigor is above a pre-set threshold. Whilst a shake cycle is in progress, an amber light emitted from the LED indicates this. Also, during a shake cycle the vibration motor emits an intermittent audible buzzing tone. The intermittent tone is set at a frequency of approximately 3 Hz to reinforce the frequency and speed of shake required for optimum mixing.

If the level of shaking vigor applied by the user drops to a level below the pre-set threshold, then the electronic system detects this using the 3-axis accelerometer. If this event has been detected, then the device enters a pause mode, which pauses the timing process and indicates to the user that the device has entered the pause mode. This indication to the user is provided by pausing the tactile vibration from the vibration motor. Upon receiving the pause indication, the user may then correct their actions, by recommencing the shake action or increasing the vigor of the shake action such that the level of shaking vigor is above a pre-set threshold. At this moment, the device switches out of pause mode and recommences with the timing and acceleration monitoring process. In this case, the time count starts from the time count at which the device was paused. If the device is in pause mode for a significant amount of time, such that the particles may have started to re-form a sediment, the timer will be reset.

Once the user has achieved sufficient vigor and time of shaking, the electronic system determines that the shake cycle is completed. The completion of the shake cycle is indicated to the user by emitting a green light from the LED. The completion of the shake cycle is also indicated to the user by the vibration motor emitting a continuous tone.

Once the shaking cycle has been completed successfully, a timer begins to count to ensure that too much time does not elapse between the shaking of the device and the administration of the injection. The timer is set such that when a maximum allowable time after shaking the housing has elapsed, the user is warned to shake the device again before administration. The timer may be set, for example, to warn the user after five minutes of inaction after shaking the housing. An indication to the user that the maximum time has elapsed is given by switching off the green light from the LED which previously indicated that the shake cycle was completed.

When the power remaining in the battery reaches a low enough level, such that the functionality of the device may soon become impaired, the device is configured to indicate to the user that a battery failure is imminent. At this point the user may replace the battery. In the event where the electronic system has detected that the power level in the battery is too low, the device is shut down, such that it may not be used until the battery has been replaced.

Upon being awoken by the user in preparation for a shake cycle, the electronic system performs self-checks on the system and the main components, such as the 3-axis accelerometer. If the electronic system determines the device to be faulty, an error mode is entered and this is communicated to the user through the LED or the vibration motor. This prevents the user from using a faulty device and prompts them to take remedial action.

Figure 27:
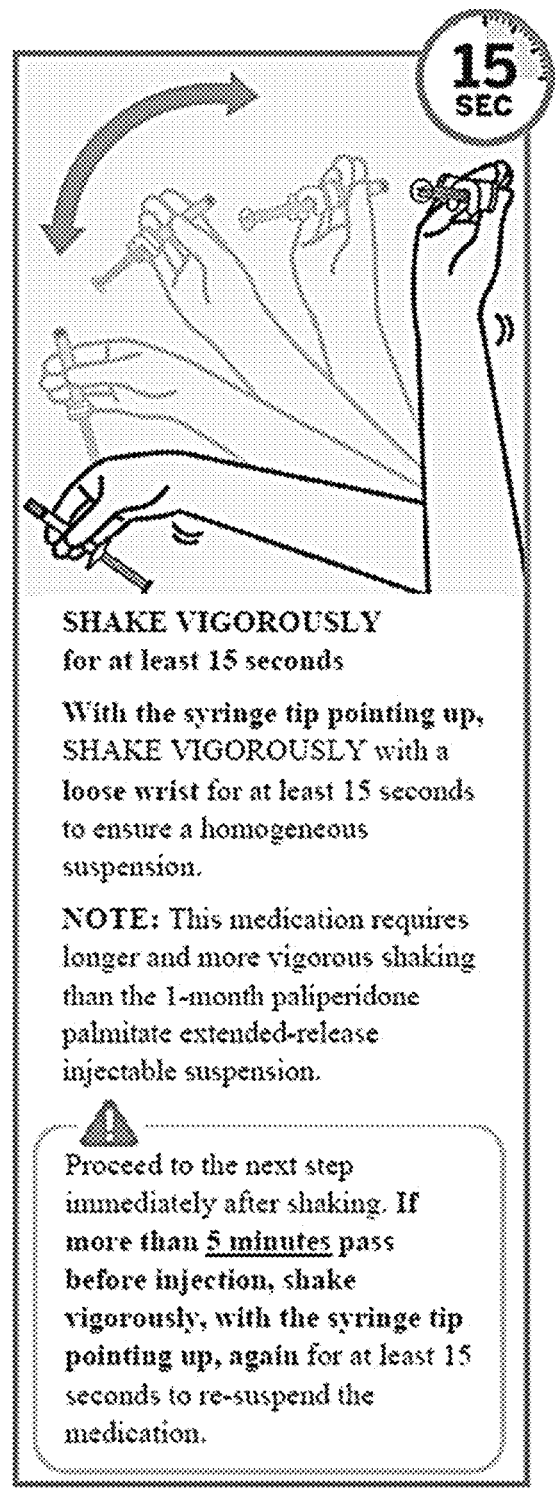
FIG. 27 is a diagram of a mixing and administration method for pharmaceutical components or drug according to the present disclosure.

Referring to FIG. 27, further information about the mixing of pharmaceutical components forming part of this disclosure is provided below.

In addition to the embodiments and disclosure provided above, which may be claimed individually, separately, in part or in combination, with features from the entire disclosure provided herein, the following numbered embodiments may be claimed individually, separately, in part or in combination, with features from the entire disclosure provided herein:

1. A device for training users in a proper mixing of pharmaceutical components or a device for aiding in the mixing and administration of pharmaceutical components, or a device for mixing and administering pharmaceutical components, the device comprising:
   a housing for receiving a pharmaceutical delivery device containing the pharmaceutical components;
   a microcontroller disposed in the housing; and a motion/orientation detection device disposed within or on the housing and in communication with the microcontroller.

2. The device of numbered embodiment 1, wherein the motion/orientation detection device is electrically connected to the microcontroller.

3. The device of any one of the preceding numbered embodiments, wherein the motion/orientation detection device comprises a device configured to detect one or both of: motion; and orientation of the housing with respect to the ground.

4. The device of any one of the preceding numbered embodiments, wherein the motion/orientation detection device is configured to detect a motion of the housing and provide a signal indicative of such motion to the microcontroller.

5. The device of any one of the preceding numbered embodiments, wherein the motion/orientation detection device is configured to detect an orientation of the housing and provide a signal indicative of such orientation to the microcontroller.

6. The device of any one of the preceding numbered embodiments, further comprising a user notification device.

7. The device of numbered embodiment 6, wherein the user notification device comprises one or more of: a display, a tactile feedback unit, a light emitting device and/or a vibratory alert unit.

8. The device of numbered embodiment 6 or numbered embodiment 7, wherein the user notification device is mounted on an external surface of the housing for notifying a user as to its status.

9. The device of any one of the preceding numbered embodiments when dependent on any one of numbered embodiments 6 to 8, wherein the microcontroller is configured to indicate via the user notification device as to whether the motion and/or orientation of the housing being shaken during one of a drug mixing and administration, or a training event, is sufficient enough for satisfactory mixing of the pharmaceutical components for delivery.

10. The device of numbered embodiment 9, wherein the user notification device is a display and the microcontroller is configured to indicate via the display the state of mixing of the pharmaceutical components in a real-time manner.

11. The device of numbered embodiment 10, wherein the microcontroller is configured to change progressively the color and or pattern of one or more display elements on the display as shaking takes place until sufficient shaking has taken place for satisfactory mixing of the pharmaceutical components for delivery.

12. The device of numbered embodiment 10, wherein the microcontroller is configured to display two types of display elements on the display which are grouped together in two discrete portions of the display prior to commencement of shaking, and which progressively mix which each other on the display so long as shaking continues at a sufficient enough or pre-defined force and/or for a sufficient enough or predefined duration, until such time that it is determined that sufficient shaking has taken place for satisfactory mixing of the pharmaceutical components for delivery, at which time the two types of display elements are wholly integrated with each other in a regular pattern across the display.

13. The device of any one of numbered embodiments 9 to 12, wherein the microcontroller is configured to determine whether there is satisfactory mixing with respect to one or more predetermined thresholds including magnitude of the force applied during shaking, the orientation of the housing and duration of such shaking.

14. The device of any one of the preceding numbered embodiments, wherein the movement/orientation detection device comprises an accelerometer.

15. The device of numbered embodiment 14, wherein the accelerometer comprises a 3-axis accelerometer.

16. The device of any one of the preceding numbered embodiments, further comprising a power source disposed in the housing.

17. The device of numbered embodiment 16, wherein the microcontroller is, when active, electrically powered by the power source.

18. The device of any one of the preceding numbered embodiments, further comprising a start switch electrically connected to the microcontroller.

19. The device of numbered embodiment 18, wherein the start switch is configured to activate the microcontroller from a power conservation mode into an active mode upon detection of movement of the housing during one of a drug mixing and administration event, or a training event.

20. The device of numbered embodiment 19, wherein the microcontroller is configured, during the power conservation mode, to draw reduced power with respect to the active mode, or no power at all, from the power source.

21. The device of any one of numbered embodiments 18 to 20, wherein the start switch is the motion/orientation detection device.

22. The device of any one of numbered embodiments 18 to 20, wherein the start switch is separate to the motion/orientation detection device.

23. The device of any one of the preceding numbered embodiments, wherein the microcontroller is configured to detect, during one of a drug mixing and administration or a training event, when shaking of the housing has ended prematurely for sufficient enough mixing of the components, or if the level of shaking vigor of the housing has reduced to a level below a pre-set threshold for sufficient enough mixing of the components, and, if so, to enter a pause mode to restart shaking.

24. The device of numbered embodiment 23, wherein the pause mode is notified to the user via the user notification device.

25. The device of any one of the preceding numbered embodiments, wherein the microcontroller is configured, during one of a drug mixing and administration or a training event, to set a timer and determine when a maximum allowable time has elapsed after sufficient shaking of the housing has completed, and is configured, if the maximum allowable time has elapsed to warn a user via the user notification device to shake the device again.

26. The device of any one of the preceding numbered embodiments, wherein the housing extends along a longitudinal axis of the device.

27. The device of any one of the preceding numbered embodiments, wherein the pharmaceutical delivery device comprises a syringe or vial.

28. The device of numbered embodiment 27, when dependent on numbered embodiment 26, wherein the housing comprises a syringe barrel element with finger flange and one end and a barrel tip spaced apart along the longitudinal axis.

29. The device of any one of numbered embodiments 27 or 28, wherein the housing comprises a body with a slot sized to accept a syringe barrel or a vial containing the pharmaceutical components.

30. The device of numbered embodiment 29, wherein the slot is aligned with the longitudinal axis of the housing, and the longitudinal axis of the syringe barrel or the vial.

31. The device of any one of numbered embodiments 27 to 30, wherein the housing is provided with a compartment and a lid to receive an entire syringe or vial.

32. The device of numbered embodiment 31, wherein the compartment is dimensioned to receive the entire syringe or vial snuggly and hold it securely within the housing.

33. The device of any one of numbered embodiments 27 to 32, wherein the housing comprises an elongated body approximately the same, or slightly greater than the length of a syringe barrel, such that a syringe is inserted into a syringe receiving hole in the body and retained by the compressive force applied by the finger-like members between a syringe finger flange and a body base.

34. The device of any one of numbered embodiments 27 to 33, wherein the housing comprises a body with a syringe accepting slot sized to accept a syringe barrel.

35. The device of any one of numbered embodiments 27 to 34, wherein the housing comprises a puck-like body with a syringe accepting hole so that, in use, a syringe is inserted into the syringe accepting hole and is held in place with a user's thumb on an underside thumb grip.

36. The device of any one of numbered embodiments 27 to 35, wherein the housing comprises an opening through which a discharge nozzle of the syringe or vial extends, or comprises an opening through which at least a portion of the syringe barrel adjacent the syringe's discharge nozzle can extend.

37. The device of any one of numbered embodiments 27 to 35, wherein the housing comprises a discharge nozzle which is adapted to be in fluid communication with the contents of a vial when such a vial is inserted into the housing.

38. The device of any one of numbered embodiments 27 to 35, wherein the syringe comprises a discharge member adapted upon application of force thereto to discharge the contents of the syringe.

39. The device of numbered embodiment 38, wherein the device further comprises an activator adapted to act upon the discharge member of the syringe, or act on the vial, to expel its contents through the discharge nozzle.

40. The device of numbered embodiment 38, wherein the housing further comprises an activator opening through which the discharge member of the syringe can extend for application of force directly by user from outside the housing.

41. The device of numbered embodiment 27, wherein the device is an attachment for a syringe and the housing is adapted to fit around a barrel of the syringe.

42. The device of numbered embodiment 41, wherein the housing is adapted to fit around only a portion of the barrel of the syringe.

43. The device of numbered embodiment 41 or 42, wherein the housing is formed of two hinged portions which rotate in a hinged manner with respect to each other, such that the hinged portions can close around the barrel and latch thereto.

44. The device of any one of the preceding numbered embodiments when dependent on any one of numbered embodiments 16 to 22, wherein the microcontroller is configured to detect low remaining power availability of the power source.

45. The device of numbered embodiment 44, wherein, when the microcontroller detects a low remaining power availability of the power source, it performs one or more of the following:
issues an alert representative of the low remaining power availability to the user, for example via a user notification device; and
prevents activation of the pharmaceutical delivery device for delivery of the pharmaceutical components to a user.

46. The device of any one of the preceding numbered embodiments, wherein the microcontroller is configured to detect an fault in the functioning of the device, for example in one or more of the motion/orientation detection device, the housing or its attachment to or containment of the pharmaceutical delivery device.

47. The device of numbered embodiment 46, wherein, when the microcontroller detects the error, it performs one or more of the following:
issues an alert representative of the error to the user, for example via a user notification device; and
prevents activation of the pharmaceutical delivery device for delivery of the pharmaceutical components to a user.

48. The device of any one of the preceding numbered embodiments, further comprising a delivery device identification unit in communication with the microcontroller.

49. The device of numbered embodiment 48, wherein the delivery device identification unit is configured to read data on data storage means of the delivery device characteristic of the pharmaceutical components contained therein and/or delivery device itself.

50. The device of numbered embodiment 49, wherein the data comprises one or more of:
expiration date of the pharmaceutical components, whereby the microcontroller is configured to alert a user via a user notification device of the device if the current date as determined by the microcontroller exceeds the expiration date;
data identifying the pharmaceutical components contained within the delivery device, for example data indicative of manufacturer or composition of the pharmaceutical components, whereby the microcontroller is configured to alert a user via a user notification device of the device if the data identifying the pharmaceutical components does not match or sufficiently correspond to permitted pharmaceutical components as stored in the microcontroller or in memory connected thereto;
expiration date of the pharmaceutical components, whereby the microcontroller is configured to prevent activation of the pharmaceutical delivery device for delivery of the pharmaceutical components to a user if the current date as determined by the microcontroller exceeds the expiration date; and
data identifying the pharmaceutical components contained within the delivery device, for example data indicative of manufacturer or composition of the pharmaceutical components, whereby the microcontroller is configured to prevent activation of the pharmaceutical delivery device for delivery of the pharmaceutical components to a user if the data identifying the pharmaceutical components does not match or sufficiently correspond to permitted pharmaceutical components as stored in the microcontroller or in memory connected thereto.

51. A method to direct a user on a proper drug mixing technique with the device of any one of claims 1 to 50, the method comprising at least the step of determining motion and/or orientation of the housing.

52. A device according to any one of claims 1 to 50, wherein one of the pharmaceutical components comprise an active pharmaceutical substance which is INVEGA TRINZA™ (see Appendix; section 11).

53. A device according to any one of claims 1 to 50, wherein one of the pharmaceutical components comprise an active pharmaceutical substance which comprises a racemic mixture of (+)- and (−)-paliperidone palmitate.

54. A device according to any one of claims 1 to 50, wherein one of the pharmaceutical components comprise an active pharmaceutical substance which is $C_{39}H_{57}FN_4O_4$.

55. The device of any one of claims 52 to 54, wherein the active pharmaceutical substance and/or device is for use in the treatment schizophrenia.

56. The device any one of claims 52 to 55, wherein at least one other of the pharmaceutical components comprises a fluid in which the active pharmaceutical substance is suspended.

57. A substance for use as one of the pharmaceutical components in the device of any one of claims 1 to 50, comprising an active pharmaceutical substance which is INVEGA TRINZA™ (see Appendix; section 11).

58. A substance for use as one of the pharmaceutical components in the device of any one of claims 1 to 50, comprising an active pharmaceutical substance which comprises a racemic mixture of (+)- and (−)-paliperidone palmitate.

59. A substance for use as one the pharmaceutical components in the device of any one of claims 1 to 50, comprising an active pharmaceutical substance which is $C_{39}H_{57}FN_4O_4$.

60. The substance of any one of claims 57 to 59 for use in the device for the treatment of schizophrenia.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

The invention claimed is:

1. A device for training or aiding users in a proper mixing of pharmaceutical components, the device comprising:
   a housing having an opening configured to receive at least a portion of a barrel of a syringe therein, the syringe being retainable within the housing by a compressive force applied between a base of the housing and a finger flange of the syringe;
   a microcontroller disposed in the housing;
   a motion/orientation detection device disposed in the housing and electrically connected to the microcontroller whereby the microcontroller is configured to detect a motion and/or orientation of the housing to train or aid users in the proper mixing of pharmaceutical components; and
   a user notification device for alerting a user to a status of the device for training or aiding users as determined by the microcontroller.

2. The device of claim 1, wherein the housing defines a major longitudinal axis.

3. The device of claim 2, wherein the housing is adapted to receive a drug delivery device having a major longitudinal axis, and further to align the longitudinal axis of the device along the major longitudinal axis of the drug delivery device.

4. The device of claim 1, wherein the microcontroller is configured to detect a motion and/or orientation of the housing with respect to motion along or about the longitudinal axis.

5. The device of claim 1, wherein the user notification device is configured to be in communication with the microcontroller and to generate user notifications under instruction from the microcontroller.

6. The device of claim 1, wherein the microcontroller is configured to detect in a shaking event whether the motion of the housing being shaken during one of a pharmaceutical administration or a training event is sufficient with respect to one or more predetermined thresholds including one or both of: magnitude of the force applied during the shaking and duration of such shaking.

7. The device of claim 1, wherein the microcontroller is configured to notify a user via the user notification device as to whether the motion or orientation of the housing being shaken during one of a pharmaceutical administration or training event is sufficient with respect to one or more predetermined thresholds including one or more of: magnitude of the force applied during the shaking; orientation of the housing; and duration of such shaking.

8. The device of claim 6, wherein the motion/orientation detection device is configured to commence detection for the shaking event upon detection of movement of the housing in excess of a predetermined level during one of a pharmaceutical administration or a training event.

9. The device of claim 6, wherein the microcontroller is configured to detect via the motion/orientation detection device one or more of the following events during the shaking event: when shaking of the housing has ended prematurely; if the level of shaking vigor has reduced to a level below the one or more pre-set thresholds; if the average level of shaking vigor over a predetermined time of the shaking event reduces to a level below one or more predefined thresholds; if the component of shaking in a predetermined direction is insufficient with respect to a predetermined level.

10. The device of claim 1, wherein the user notification device comprises one or more of: a display, a tactile feedback unit, a light emitting device, and/or a vibratory alert unit.

11. The device of claim 10, wherein the microcontroller is configured to generate a user notification comprising a color and/or pattern in the user notification device as shaking takes place mixing or simulated mixing of the pharmaceutical components for delivery.

12. The device of claim 11, wherein the microcontroller is configured to change a color and/or pattern of one or more user notifications of the user notification device as shaking takes place until sufficient shaking has taken place for satisfactory mixing or satisfactory simulated mixing of the pharmaceutical components for delivery.

13. The device of claim 1, wherein the motion/orientation detection device comprises a 3-axis accelerometer which is configured to detect a component of shaking acceleration in each of three tangential directions and provide data indicative of the components to the microcontroller.

14. The device of claim 1, in which the housing comprises an elongated body approximately the same length as the syringe barrel.

15. The device of claim 1, in which the housing comprises a puck-like body.

16. The device of claim 1, comprising a power source disposed in the housing and electrically connected to the microcontroller.

17. The device of claim 1, wherein the motion/orientation detection device is an accelerometer.

18. The device of claim 1, wherein the pharmaceutical components comprise at least two phases.

19. The device of claim 18, wherein at least one of the two phases is a solid phase and at least one of the two phases is a liquid phase.

20. The device of claim 18, wherein two of the at least two phases are liquid phases.

\* \* \* \* \*